United States Patent [19]
Carter

[11] Patent Number: 5,899,911
[45] Date of Patent: May 4, 1999

[54] METHOD OF USING NEEDLE-POINT SUTURE PASSER TO RETRACT AND REINFORCE LIGAMENTS

[75] Inventor: James E. Carter, Dana Point, Calif.

[73] Assignee: Inlet Medical, Inc., Eden Prairie, Minn.

[21] Appl. No.: 08/985,695

[22] Filed: Dec. 5, 1997

Related U.S. Application Data

[63] Continuation-in-part of application No. 08/608,297, Feb. 28, 1996, Pat. No. 5,827,299, which is a continuation-in-part of application No. 08/139,637, Oct. 19, 1993, Pat. No. 5,507, 758, which is a continuation-in-part of application No. 08/112,585, Aug. 25, 1993, Pat. No. 5,496,335.

[51] Int. Cl.$^6$ ..................................................... A61B 17/04
[52] U.S. Cl. ......................... 606/148; 606/139; 606/144; 606/145; 606/151
[58] Field of Search ................................... 606/148, 139, 606/144, 145, 151

[56] References Cited

U.S. PATENT DOCUMENTS

| 5,015,250 | 5/1991 | Foster ....................................... 606/147 |
| 5,222,508 | 6/1993 | Contarini ................................. 128/898 |
| 5,496,335 | 3/1996 | Thomason et al. ...................... 606/148 |
| 5,827,299 | 10/1998 | Thomason et al. ...................... 606/148 |

*Primary Examiner*—Michael Buiz
*Assistant Examiner*—Tina T. D. Pham
*Attorney, Agent, or Firm*—Cislo & Thomas LLP

[57] ABSTRACT

A surgical instrument, guide, and method capable of being used for closure of peritoneum fascia, occlusion of bleeding vessels such as inferior epigastric, and for all uses related to accurately passing suture material through a guide into tissue. A tip of a surgical instrument in a standard suture-/needle-driving position with a sharp tip that opens and closes with the surgeon grasping suture material with the sharp tip is provided. Insertion of the tip/suture through tissue until the tip is seen through the peritoneum by direct vision begins the wound-closing procedure. The suture is released by opening and withdrawing the tip from the guide. The suture is recovered by using the guide to redirect the tip and puncturing the tissue opposite the first point of insertion. The tip grasps the suture and pulls the suture through the guide. The suture is pulled outside the wound, providing for rapid closure of the surgical incision. The guide is insertable within the wound to be closed and guides the surgical instrument at a predetermined angle from the longitudinal axis of the guide for optimum wound closure. The surgical instrument and method may be used to advantageously shorten and strengthen ligaments. For example, by gathering and reinforcing the round ligament that supports a woman's uterus with suture materials, surgeons can reposition and stabilize a retroverted uterus.

19 Claims, 19 Drawing Sheets

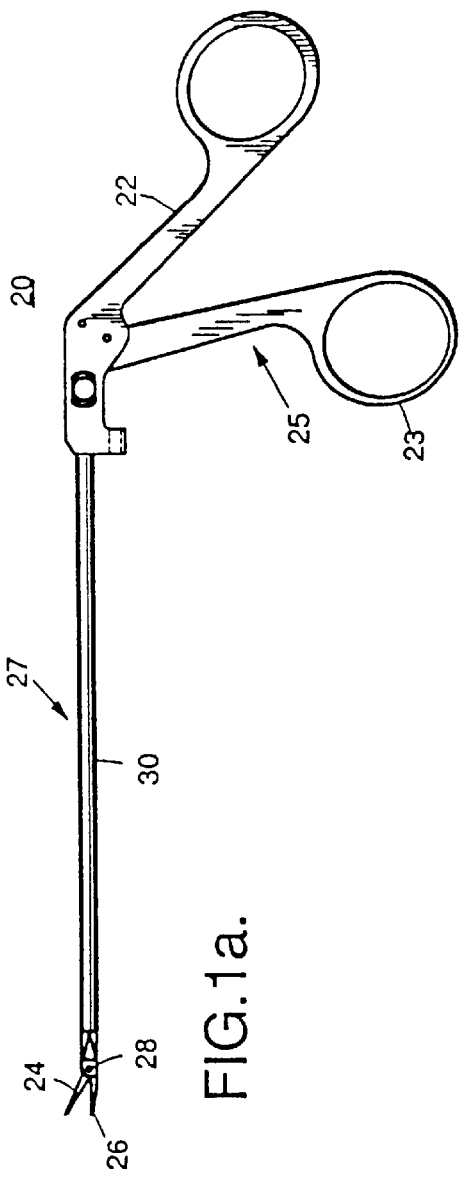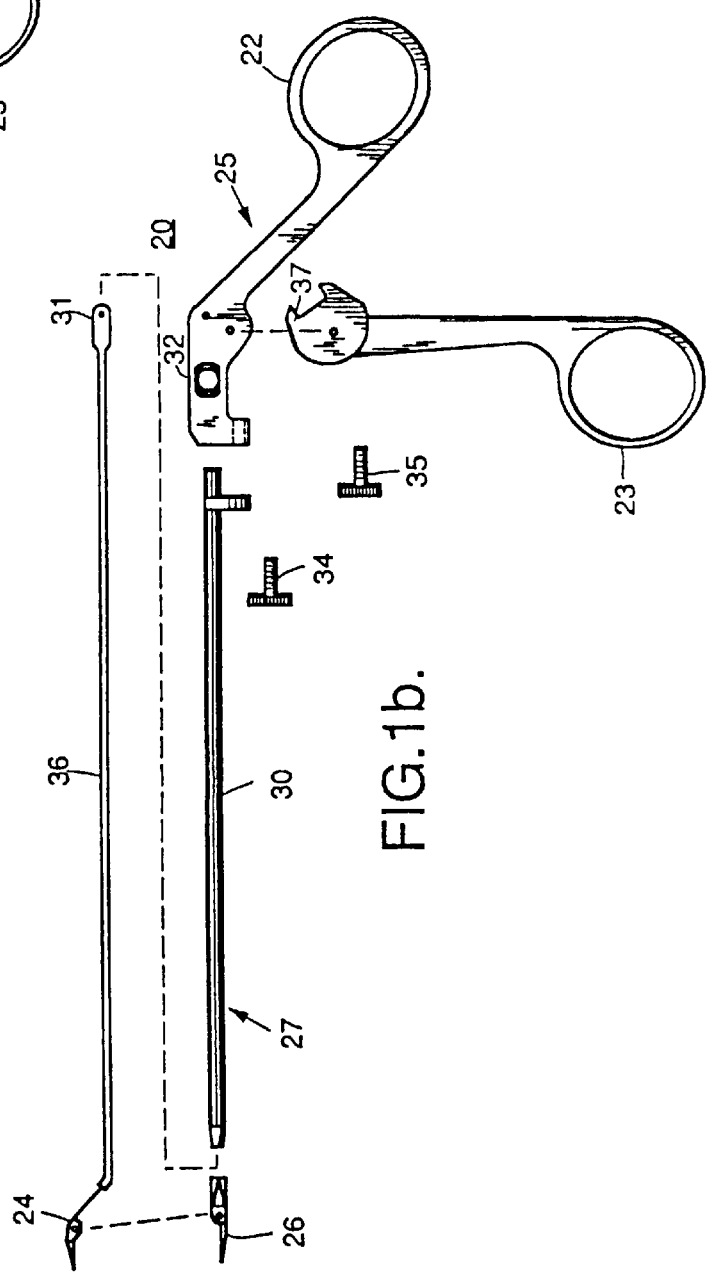
FIG.1a.
FIG.1b.

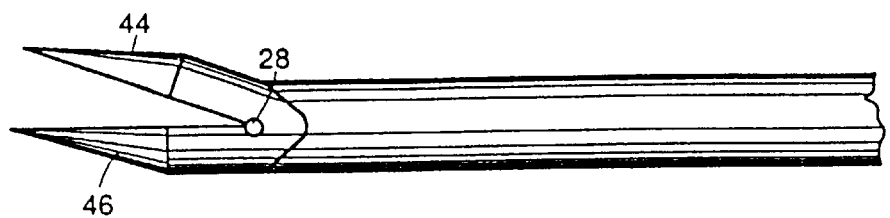
FIG. 7.
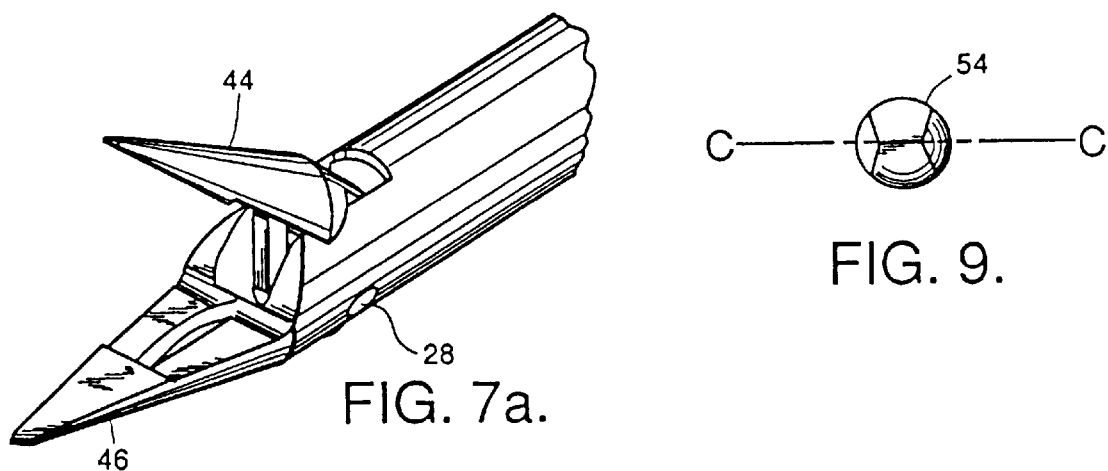
FIG. 7a.
FIG. 9.
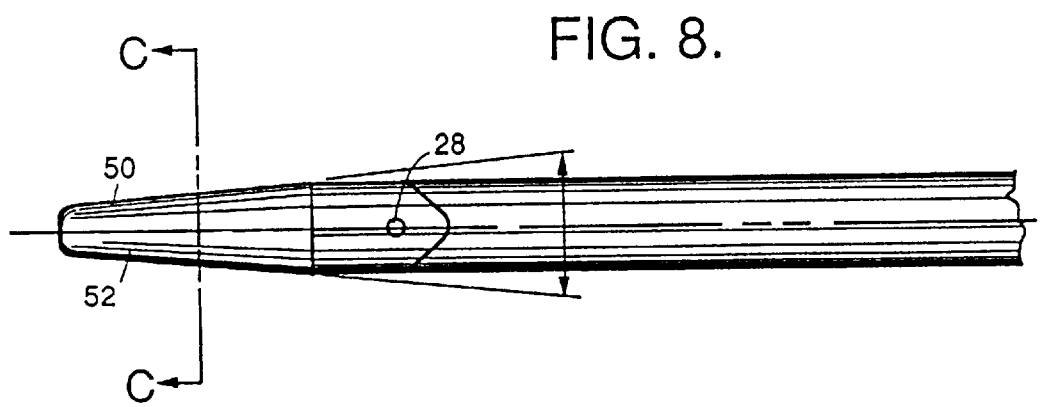
FIG. 8.
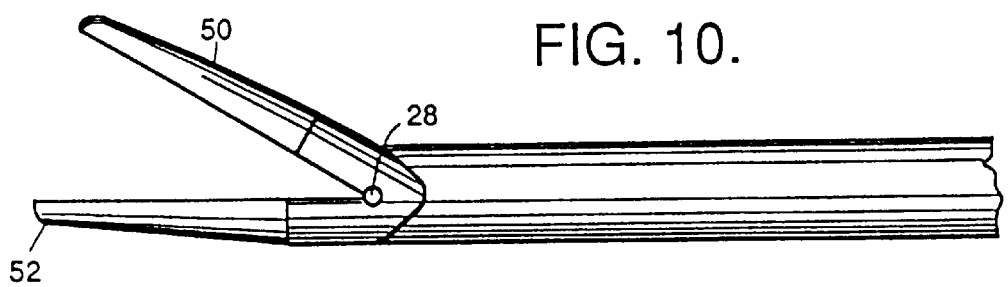
FIG. 10.

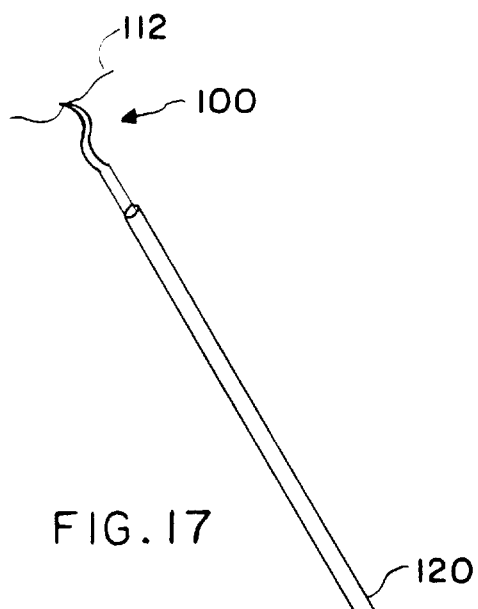
FIG. 17
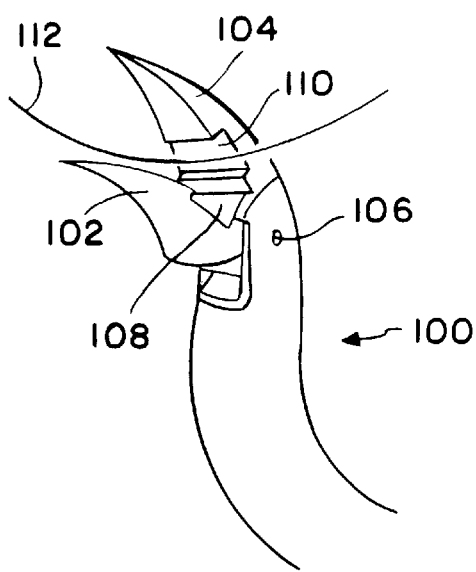
FIG. 15
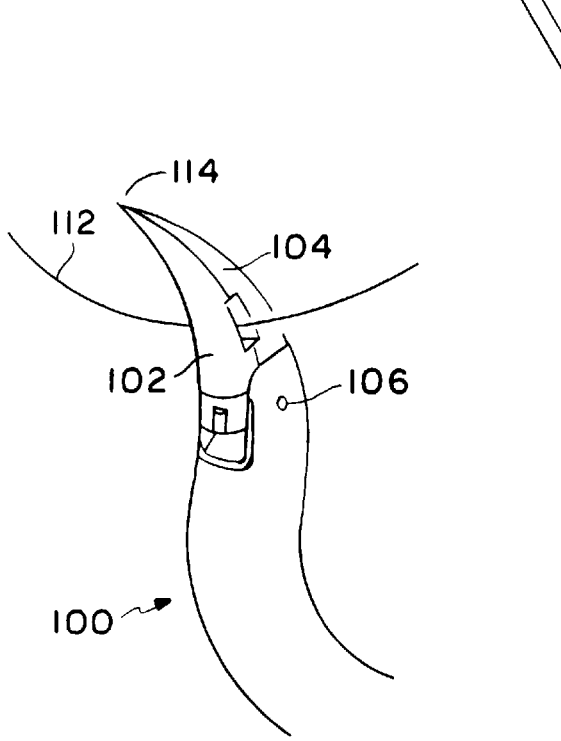
FIG. 16
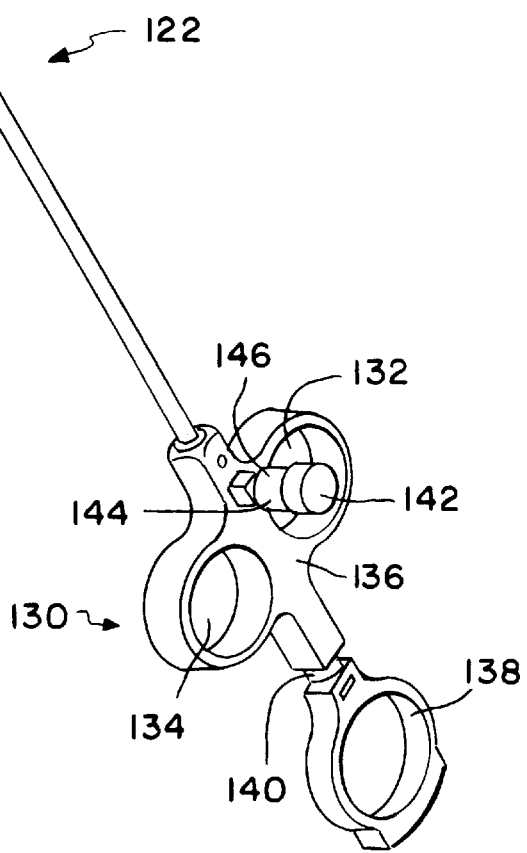

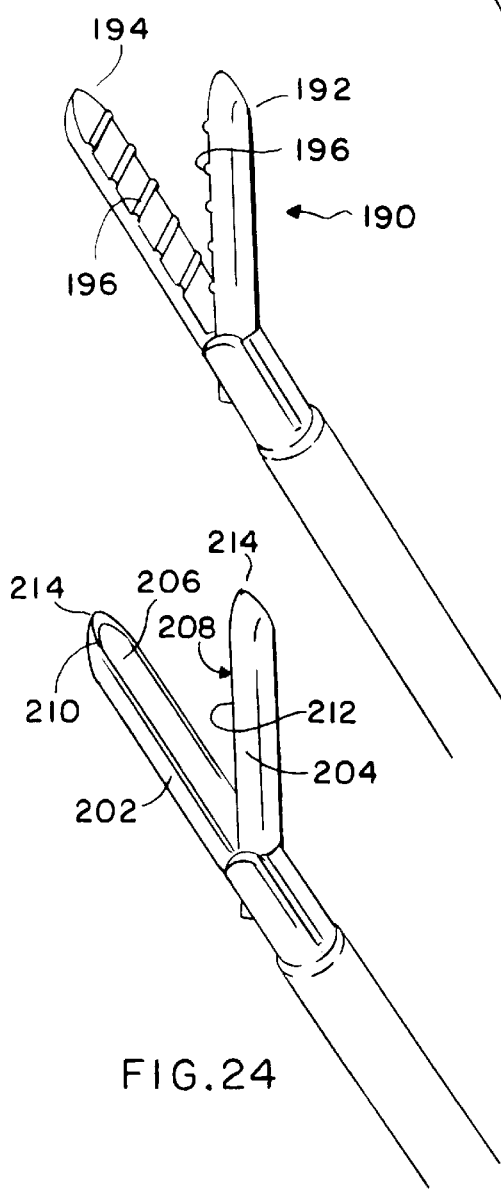
FIG. 23
FIG. 24
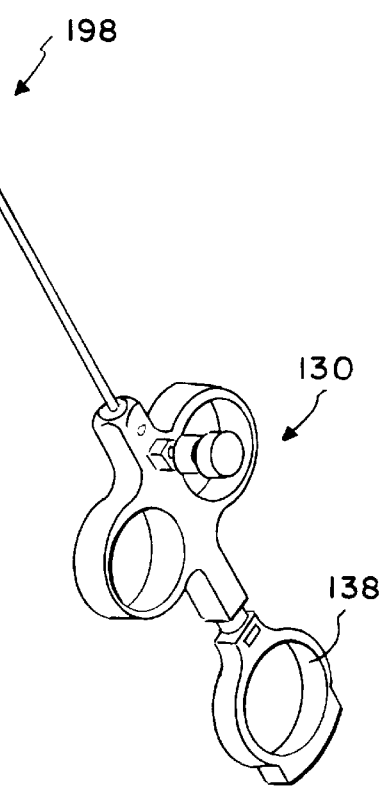
FIG. 25

METHOD OF USING NEEDLE-POINT SUTURE PASSER TO RETRACT AND REINFORCE LIGAMENTS

CROSS-REFERENCES TO RELATED APPLICATIONS

This application is a continuation-in-part of U.S. patent application Ser. No. 08/608,297 filed Feb. 28, 1996, now U.S. Pat. No. 5,827,299, which is a continuation-in-part of U.S. application Ser. No. 08/139,637 filed Oct. 19, 1993, now U.S. Pat. No. 5,507,758 which is a continuation-in-part of U.S. patent application Ser. No. 08/112,585 filed Aug. 25, 1993, now U.S. Pat. No. 5,496,335.

BACKGROUND OF THE INVENTION

1. Field of the Invention

The present invention relates to improvements in the procedure for suturing tissue during endoscopic/laparoscopic surgery, and to a method of suturing which utilizes a modified laparoscopic grasper and a guide. More particularly, the improved method relates to suturing of ligaments using a needle-point suture passer to retract and reinforce the ligaments, applications including uterine suspension and positioning.

2. Description of the Related Art

An endoscopic/laparoscopy procedure involves making small surgical incisions in a patient's body for the insertion of trocar tubes thereby creating access ports into the patient's body. Thereafter, various types of endoscopic/laparoscopic instruments are passed through these access ports and the appropriate surgical procedures are carried out.

After the surgical procedure is performed, the trocar tubes are removed and the incisions sutured closed by using both a needle and grasper for penetrating the tissue and handling the suture. This procedure for closure is frequently a time-consuming procedure requiring the identification of the fascia and closure of each fascial site with suture from an external point.

The necessity for closing these port sites in laparoscopic surgery is critical since suturing the incisions improperly can lead to bowel herniation through the port sites as well as the possibility of mental trapping if the fascial sites are not properly closed. Incisional hernias have occurred in both laparoscopic-assisted vaginal hysterectomies and laparoscopic cholecystectomies as well as other advanced laparoscopic procedures.

Thus there is a need for an endoscopic/laparoscopic instrument and method which will significantly reduce the operating time and is better able to give the surgeon direct visualization of the fascial and peritoneal closing. Additionally, there is a need for a surgical instrument which allows the surgeon to control bleeding sites by rapidly putting sutures around blood vessels of the abdominal wall.

Furthermore, there is a need to accurately and consistently guide and orient an endoscopic/laparoscopic instrument into proper position to accurately and easily provide for placement and retrieval of suture materials within an open wound to be closed.

The subject invention herein solves all of these problems in a new and unique manner which has not been part of the art previously. General types of surgical forceps and laparoscopic graspers are known in the art, and some related patents directed to surgical instruments or guides are described below:

U.S. Pat. No. 5,192,298 issued to W. Smith et al. on Mar. 9, 1993

This patent is directed to a disposable laparoscopic surgical instrument. The laparoscopic surgical instrument comprises a tube surrounded by a peripheral insulating shrink-wrap layer, a clevis means, effectors pivotally engaged to the clevis at a pivot pin, and activating means. The effectors are provided with blades or graspers which taper to a point and are rotatably mounted on the pivot pin.

U.S. Pat. No. 5,201,743 issued to T. Habeir et al. on Apr. 13, 1993

This patent is directed to an axially extendable endoscopic surgical instrument. The endoscopic surgical instrument includes an elongate body, a tip carrier tube, a tip assembly removably mounted to the distal end of the carrier tube and having a pair of movable jaws, a driver assembly which causes jaws to move between open and closed positions, and a jaw-rotating assembly which causes the tip assembly and jaws therewith to rotate about an axis. The jaws taper substantially at their distal ends, and the interior surface of the jaws are serrated.

U.S. Pat. No. 4,950,273 issued to J. M. Briggs on Aug. 21, 1990

This patent is directed to a cable-action instrument. The instrument comprises a controller, a reaction end, and an angle adjustment section which connects the controller to the reaction end, and a flexible control cable assembly extending between the controller and the reaction end. The reaction end consists of a scissors tip having a stationary blade and a cable-activated blade, both of which have pointed distal ends. A forceps instrument tip having a stationary plant arm and a cable-activated arm may be substituted for the scissors tip.

U.S. Pat. No. 4,938,214 issued to P. Specht et al. on Jul. 3, 1990

This patent is directed to a hand-held surgical tool. The surgical tool includes an operating end having first and second blade tips which are movable between open and closed positions. When the blade tips are closed, the surgical tool has a needle-sharp point having a diameter of only about 50 microns to 2 mm.

U.S. Pat. No. 3,577,991 issued to G. R. Wilkinson on May 11, 1971

This patent is directed to a tissue-sewing instrument, the forceps are pivoted together with the outer jaws and a spring set between the members. The thread slides to the end of the forceps, and the free end of the thread is pulled through the loops to make a knot.

U.S. Pat. No. 5,196,023 issued to W. Martin on Mar. 23, 1993

This patent is directed to a surgical needle holder and cutter wherein the cutter forming the upper part of the blade has a concave shape. When the forceps jaw is opened, an approximately elliptical opening is formed between the ridge, or cutter, and the depression into which a thread may be brought from the direction of the opening of the forceps jaw and then can be cut off by closing the jaw.

U.S. Pat. No. 5,222,508 issued to O. Contarini on Jun. 29, 1993

This patent is directed to methods for closing punctures and small wounds of the human body, allowing such punctures to be sutured and closed with an internal seal. Before the trocar is removed, a suture insertion means, a needle preferably of stainless steel, having an eyelet or a slot or barb to retain the suture material, is pushed completely through the skin and subcutaneous layer. A retrieval means is inserted adjacent the puncture so its barbed portion grasps or snares the free end of the suture material. The insertion needle, retrieval needle, and trocar are withdrawn and the suture drawn tight.

U.S. Pat. No. 5,053,043 issued to J. Gottesman et al. on Oct. 1, 1991

This patent is directed to a suture guide with interchangeable tips for placing sutures in the severed end of a body duct. Various tips having one or more apertures and channels for placing sutures are provided to screw into an elongate member. The elongate member has a handle at the opposite end. This guide is particularly useful for the placement of sutures into the urethral stump.

U.S. Pat. No. 5,201,744 issued to M. W. Jones on Apr. 13, 1993

This patent is directed to a method and device for suturing using a rod with a needle holder. This device, a knot-tier instrument, has a rod with an end having notches for guiding suturing threads, and a slot for holding a needle. The end may be magnetized to aid in magnetically holding the needle in the slot. A hollow cannula, or access tube, can be inserted through the skin, and the knot tier inserted into the cannula for suturing the wound closed.

U.S. Pat. No. 5,176,691 issued to J. Pierce on Jan. 5, 1993

The patent is directed to a plurality of embodiments of knot pushers formed from elongated rods. The pusher with an elongated rod has various configurations to guide suture ends and push the knot. The end of the rod has a face shaped to push the knot, and near the edges of the rod are eyelets or grooves or the like to guide the sutures as the knot is being pushed. The purpose of the device is to advance the knot of a suture through an endoscope portal or a cannula or the like.

U.S. Pat. No. 4,621,640 issued to J. S. Mulhollan on Nov. 11, 1986

This patent is directed to a mechanical needle carrier which can grasp and carry a surgical needle through a cannula, position the needle, and set a stitch at a remote location, then release the needle for withdrawal from the cannula. The mechanical needle carrier is inserted through the cannula, and a pivotal needle-carrying head is positioned by adjusting knurled knobs so as to position the needle as required. Once the needle is set, it can be released and then retrieved by forceps or the like. This mechanical needle carrier provides the structure for suturing in a restricted field with the manipulation remote from the location of the needle.

Intra-abdominal suturing is a time-consuming process for surgeons in part because a lot of manipulation and "fiddling" is associated with the needle attached to the suture material. For instance, the needle and suture material must be aligned so they can pass through a trocar sleeve. As curved needles will only fit through large trocar sleeves, larger wounds must be made for the trocars in order to pass the curved needles into the body cavity. Once inside the abdominal cavity, the needle has to be grasped, regrasped, aligned, and realigned in the needle driver. After each stitch, the needle has be to be grasped and realigned in the needle driver.

With the present invention, the needle driver and the needle are one and the same. Therefore, the disadvantages presented by having an independent needle are avoided. Suturing can start immediately without the frustration of continually realigning the needle when it is regrasped. The surgeon simply passes the suture through the tissue then, by either using the same instrument or a standard grasper, picks up the suture for tying or passing through the tissue to create another stitch for wound closure. The present invention allows introduction of suture directly through tissue or through small trocar sites, as the diameter of the shaft and its tip for the probe is generally much smaller than the average trocar. Additionally, the technique for using the present invention is easily learned; and the several embodiments set forth herein generally reduce the time and frustration associated with intra-abdominal suturing. These advantages are enhanced by use of the guide disclosed herein.

Laparoscopic surgical procedures have been used in attempts to correct misalignment of a woman's uterus. This misalignment is most often seen as a retroverted, backward-bending uterus, but can also be an anterior misalignment where the uterus is situated more towards the front than is desired. Symptoms reported as a result include chronic pelvic pain, pain on intercourse, debilitating pain during menstrual cycles, urinary problems, bowel problems, infertility and back pain.

It has been found that repositioning the uterus to a more midline position in the pelvis relieves symptoms in a great percentage of these patients. To that end a number of surgical procedures have been attempted to perform the correction.

The corrections revolve around surgeon's observations that ligaments, or tough bands of tissue which normally function to hold the uterus in a neutral position, are or have become stretched, thinned or loosened from their attachment points. Procedures designed to shorten and/or reattach these ineffective ligaments include the following:

Gilliams Procedure

The Gilliams procedure was designed to remove a section of the ligament and suture the ends back together. The resulting shortened ligaments provide more tension to hold the uterus in a neutral position. Among the drawbacks to Gilliams procedure is that it does nothing to improve the strength of thinned ligaments and they may again stretch so that the correction would be short lived. Additionally, Gilliams procedure can change the geometry of the lower pelvis when ligaments are reattached to the anterior abdominal wall, creating a pouch that may entrap the bowel which is a serious complication.

Webster-Baldy Procedure

The Webster-Baldy procedure creates a new attachment point for one ligament by passing it through another and suturing it to the wall of the lower uterine corpus.

This stretching of the ligament to a second attachment point on the uterus creates more tension with which to hold the uterus. This correction does not take advantage of the thickest part of the ligament which is the part already attached to the uterus. Changing the attachment point does nothing to improve the strength of these thinned ligaments and they may be prone to restretch.

Mann-Stenger Uterine Suspension, Candy's Modified Gilliam Uterine Suspension, Pereyra Needle Uterine Suspension, Doleris's Procedure The above procedures rely on passing suture one or more times around or through the ligament and then directly attaching the loose ends of suture to the abdominal wall for the purpose of putting more tension on the ligaments that support the uterus. The procedures do not reinforce thinned ligaments which may stretch and loosen from the fixation. They also create a cavity-like space in the anterior cul-de-sac where bowel intussusception will be most likely to occur. This may lead to a slipping of a length of intestine into an adjacent portion, which may produce an obstruction.

In contrast, the present invention uses a needle-point suture passer to carry and withdraw suture longitudinally into the ligament from a point at or near the ligament's original fixation point. Using this method, the thinned part of the ligament is reinforced with permanent suture, thus significantly reducing the risk of additional stretching. By tunneling into the ligament from the area near the natural attachment point, the natural geometry of the lower pelvis is preserved which reduces the risk of complications.

SUMMARY OF THE INVENTION

The present invention is directed to a suturing method using an improved laparoscopic surgical instrument which permits a surgeon to pass suture without trauma through tissue while retaining the function of grasping the suture. The laparoscopic surgical instrument comprises a modified laparoscopic grasper wherein forceps jaws at the tip are manipulated by means of handles extending from a tubular housing with an enclosed reciprocating actuating rod connected with the handles. As contemplated in the present invention, scissor-type or syringe-type handles may be used. In an alternative embodiment, a cannula may be used.

The laparoscopic surgical instrument of the present invention has the tip of the forceps jaws modified to have either a knife-, chisel-, or cone-shaped tip when the jaws are in the closed position. These tips are configured such that they are needle sharp which is critical in reducing trauma and accompanying bleeding and further decreases tissue damage during the suturing procedure. Other tip configurations include curved and bent tips, which allow greater facility under certain conditions. Additionally, a suture probe guide delivering guided access to appropriate tissue layers for suturing is provided.

The method of the present invention to shorten and strengthen a ligament includes entering the person's body with a surgical tool having a sharp tip and bearing suture material, and inserting the tool into the ligament and pushing the suture material along the axial length of the ligament. Then the method includes pulling the suture from outside the ligament causing the ligament to retract along its length, and incorporating the suture material such that the ligament is retracted and reinforced. The resulting ligament is shorter, thicker and stronger, and better able to support internal organs such as a woman's uterus.

OBJECTS OF THE INVENTION

It is an object of the invention is to provide a surgical method for the closure of a surgical incision under direct camera laparoscopic vision of the surgeon, and the closure that is accomplished is a mass closure which allows for closure of peritoneal surfaces as well.

A further object of the invention is to provide a laparoscopic instrument that allows for the rapid control of bleeding from inferior epigastric lacerations or other lacerations of vessels in the outer (or abdominal) wall that may occur with placement of the laparoscopy trocars.

Another object of the invention is to provide a laparoscopic instrument that easily disassembles at the handle and at the interface between the tube member and handle for providing easy access to all the instrument components for cleaning and sterilization prior to surgery.

Still another object of the invention is to provide a laparoscopic instrument having a pair of independently operated actuatable means such that a single instrument can simultaneously perform both the functions of a needle and grasper during laparoscopic surgery.

Yet another object of the present invention is to provide a surgical instrument that works in a manner similar to a needle driver without the requirement for the needle itself in passing suture easily through the fascial and peritoneal surfaces and for retrieving the suture for completing the suture procedure in a rapid, safe, and visualized manner.

It is another object of the invention to provide a guide to accurately and consistently restrain the position and angle of insertion of a laparoscopic instrument to provide for proper placement and retrieval of suture material at a predetermined location within the body.

Accordingly, it is an objective of the present invention to provide a method associated with an improved surgical instrument of the standard laparoscopic-type grasper that better suits the needs of a surgeon when suturing closed a surgical incision. In addition, it is the objective of the present invention to allow the passage of suture through tissue in order to suture or ligate vessels, approximate tissues, and perform all suturing that would require a separate needle driver in laparoscopic surgery.

Another object of the invention is to provide a method of laparoscopically inserting a suture within a ligament in a person's body, causing the ligament to retract along its length and reinforcing the ligament.

Still another object of the invention is to provide a method of laparoscopically suturing the round ligament that supports a woman's uterus to shorten and strengthen the ligament, to reposition and stabilize a misaligned uterus.

Finally, still another object of the invention is to provide a method of laparoscopically suturing the round ligament that supports the woman's uterus and anchoring the same to a bone, to reposition the uterus.

The improvements afforded by this instrument and methods will be set forth throughout the following description, claims, and accompanying drawings.

BRIEF DESCRIPTION OF THE DRAWINGS

The above, as well as other, advantages of the present invention will become readily apparent to those skilled in the art from the following detailed description of the preferred embodiments when considered in light of the accompanying drawings in which:

FIG. 1a is a side elevational view of an instrument of the present invention.

FIG. 1b is an exploded side elevational view of the instrument of FIG. 1a.

FIG. 7 is a side elevation view, partly in section, of the forceps jaws of FIG. 5 in a completely open condition.

FIG. 7a is a top right perspective view of the forceps of FIG. 7.

FIG. 8 is a side elevation view, partly in section, of the forceps jaws having a knife-shaped tip.

FIG. 9 is a cross-sectional view taken along the line C—C in FIG. 8.

FIG. 10 is a side elevation view, partly in section, of the forceps jaws of FIG. 8 in a completely open condition.

FIG. 15 is a side perspective view of a curved tip for use in the present invention, the forceps jaws shown in the open position.

FIG. 16 shows the curved tip of FIG. 15 with the forceps jaws closed.

FIG. 17 shows a perspective view of an embodiment of the present invention with the curved tip shown in FIGS. 15 and 16 holding suture.

FIG. 23 shows an embodiment of a tissue-grasping tip for use in the present invention.

FIG. 24 shows an embodiment of a biopsy tip for use in the present invention.

FIG. 25 shows a probe for use with the tips of FIGS. 23 and 24, the probe having a syringe-type handle.

DESCRIPTION OF THE PREFERRED EMBODIMENTS

Figure 2:
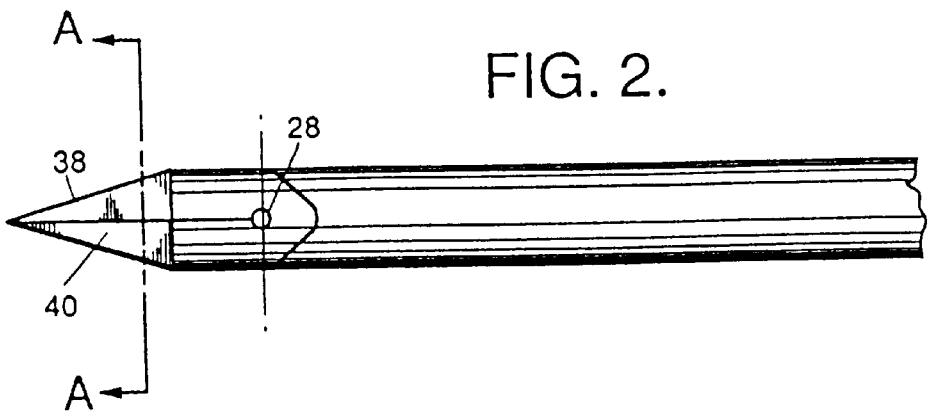
FIG. 2 is a side elevation view, partly in section, of the forceps jaws having a chisel-shaped tip.

Referring now to the drawings wherein like reference numerals refer to like and corresponding parts throughout, the laparoscopic instrument is generally indicated by numeral 20. Referring now to FIGS. 1a and 1b, forceps jaws 24 and 26 are pivoted back and forth in double-action movement about an axis defined by pivot pin 20 when actuating rod 3G is reciprocated by a surgeon manipulating the scissor handles 22 and 23 providing a driving means 25 for driving forceps jaws 24 and 26 in a closed position through a patient's skin. Detachable means 27 comprise an elongated tube 30 concentrically sharing an axis with the actuating rod 36 having forceps jaws 24 and 26 engaged at a distal end.

As shown in FIG. 1b, the laparoscopic instrument 20 may be easily disassembled for sterilization prior to surgery by separating driving means 25 from detachable means 27 by loosening the knurled screw 34 on fixed handle housing 22, rotating the elongated tube 30 and forceps jaws 24 and 26 slightly, and unlatching hook 31 from pin 37 which thereby frees actuating rod 36 and tube 30 from handle housing 22. By loosening thumb screw 35, movable handle or lever means 23 can be disassembled from fixed handle housing 22 that allows for cleaning of the inside of the handle-housing area. When disassembled, the parts may be flushed, washed, and dried according to hospital procedures for stainless steel surgical instruments. A clearing port 32 may be provided for ease in flushing the disassembled fixed handle housing 22.

Figure 3:
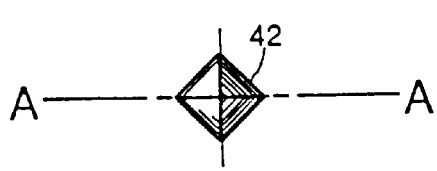
FIG. 3 is a cross-sectional view taken along the line A—A in FIG. 2.
Figure 4:
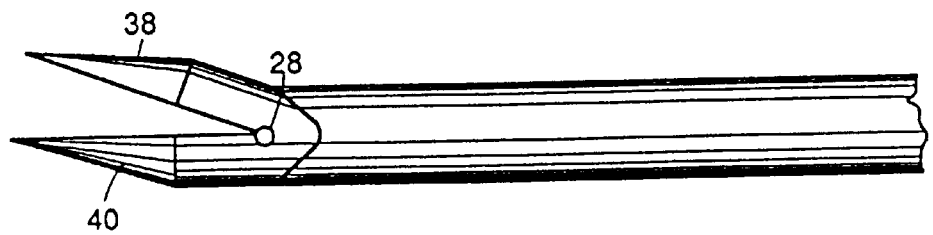
FIG. 4 is a side elevation view, partly in section, of the forceps jaws of FIG. 2 in a completely open condition.

With the above-described arrangement, it will be seen that the surgeon is able to selectively operate the scissor handles 22 and 23 to independently open and close the movable forceps jaw 24 in relationship to fixed forceps jaw 26 for grasping, carrying, or releasing suture during a laparoscopic operation. To open forceps jaw 24, the surgeon moves movable handle or lever means 23 forward toward the distal end of tube 30. As shown in FIG. 2 and 3, the forceps jaws 24 and 26 have a chisel shape 30 and 60 which, when closed, form a chisel-shape tip 42. This chisel-shape tip 42 operates as a sharp needle point that simultaneously grips and passes the suture through soft tissue. Referring to FIG. 4, chisel-shaped jaw 38 pivots open and closed about pivot pin 28 and chisel-shaped jaw 40 which is fixed and non-pivotable.

Figure 6:
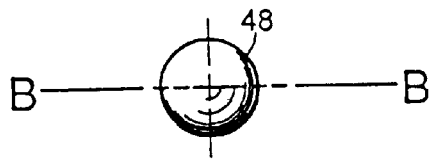
FIG. 6 is a cross-sectional view taken along the line B—B in FIG. 5.
Figure 5:
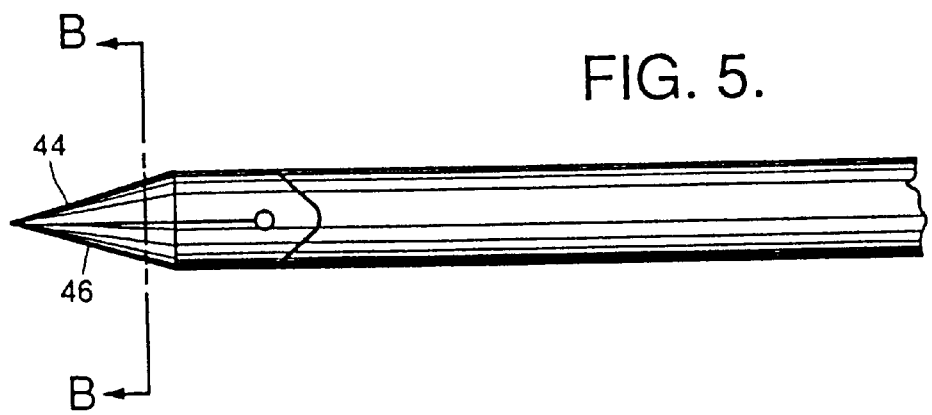
FIG. 5 is a side elevation view, partly in section, of the forceps jaws having a cone-shaped tip.

Although the forceps jaws are shown as chisel shaped in FIGS. 2 and 3, they may alternatively have a cone shape 44 and 46, forming a cone-shaped tip 48 as shown in FIG. 5 and 6. Referring to FIG. 7, cone-shaped jaw 44 also pivots open and closed about pivot pin 28 and cone-shaped jaw 46 which is fixed and non-pivotable. Alternatively, the aforementioned forceps jaws may have individual knife-shaped tips 50 and 52 forming a knife-shaped tip 54 as shown in FIGS. 8 and 9. Likewise, as shown in FIG. 10, the knife-shaped jaw 50 pivots open and closed about pivot pin 28 and knife-shaped jaw 52 which is fixed and non-pivotable. In all the above views, the tips are required to be sharp which is critical in reducing trauma and accompanying bleeding and in decreasing tissue damage during the suturing procedure.

Figure 11:
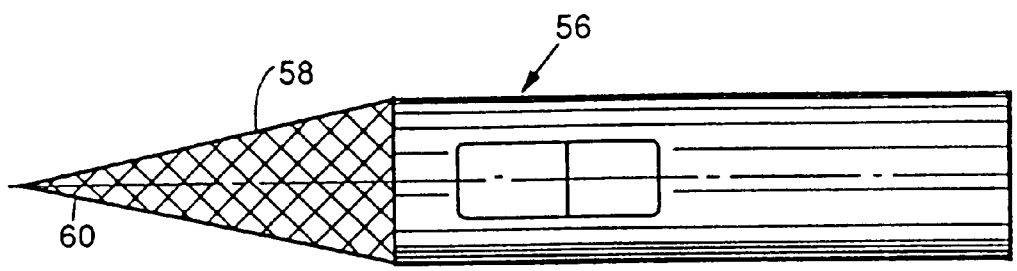
FIG. 11 is a top planar view of the bottom forceps jaw according to one embodiment of the invention.

Common to the variously shaped jaw embodiments is a generally partial crosshatched interior jaw surface 58 embedded in jaw body 56, as shown in FIG. 11, which facilitates in grasping more securely the suture material 66 during insertion into tissue. In order to maintain the sharpness of the tip, a partial nonhatched area 60 is provided at the forward end of jaw body 56.

Figure 12:
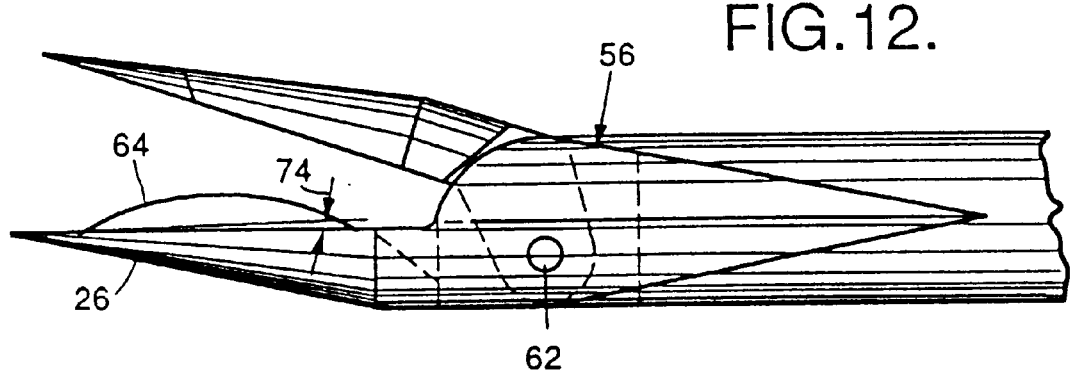
FIG. 12 is a side elevational view, partly in section, of the forceps jaws according to one embodiment of the invention.
Figure 13:
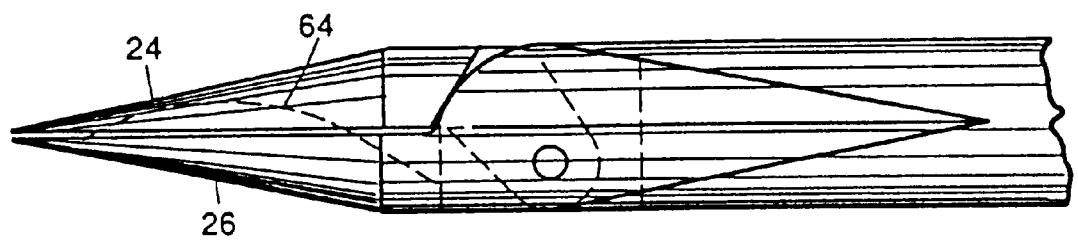
FIG. 13 is a side elevational view of the forceps jaw of FIG. 12 in a completely closed position.
Figure 13A:
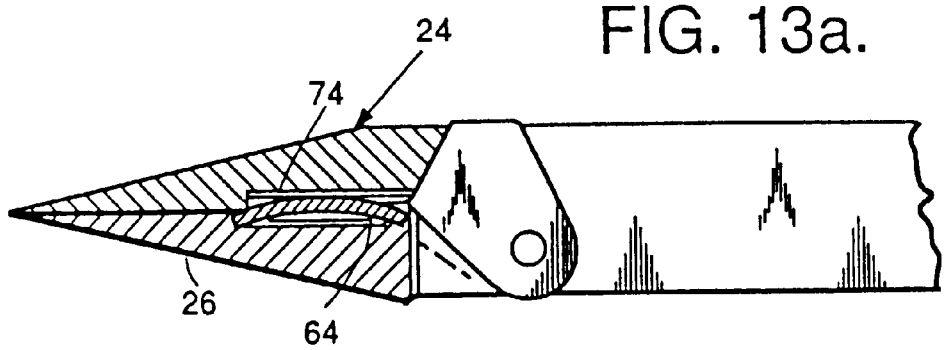
FIG. 13a is a cross section of the forceps shown in FIG. 13.

FIGS. 12 and 13 show another embodiment of a means to retain the sharpness of the tip at the end of jaw body 56 when the forceps jaws are closed. In FIG. 12 it is seen that lower forceps jaw body 26 is inclined by a small angle, indicated at 74, toward pivot-pin hole 62. With this arrangement the small angle 74 accounts for the thickness of the suture such that, when the jaws are closed, a sharp tip is still defined with the suture grasped resulting from the clearance provided by small angle 74. Additionally, a spring 64 is provided which has one end affixed into jaw body 26 at a point near pivot-pin hole 62. The spring 64 assists in more firmly grasping the suture material by adding a compression force resulting in a more positive grip when the jaws 24 and 26 are closed as shown in FIGS. 13 and 13a. The spring 64 is especially useful in handling suture material that is large in diameter, therefore allowing for a wider range of suture sizes that can be used during surgery.

These features and their advantages in use will be more particularly appreciated when reviewing the following method of the present invention used to pass suture through soft tissues during endoscopic/laparoscopic surgery for which the instrument 20 of this invention is provided. In application the surgical instrument 20 is to be grasped by a skilled laparoscopic surgeon and placed for closure of punctured vessels in the muscular surface or for closure of the fascia and peritoneum.

Figure 14A:
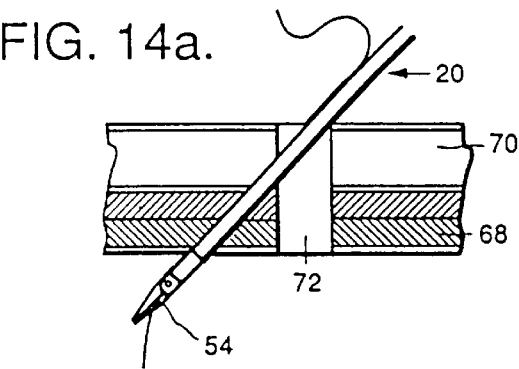
FIG. 14a is a diagrammatic sketch, partly broken away, of the tip of the surgical instrument in the closed position passing suture through tissue.
Figure 14B:
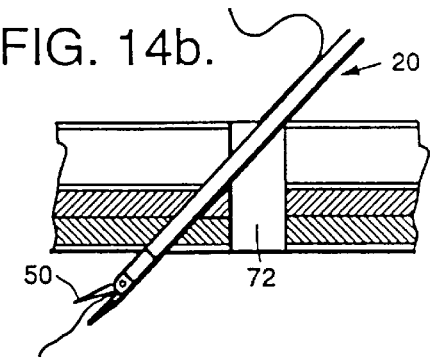
FIG. 14b is a diagrammatic sketch, partly broken away, of the tip of the surgical instrument in the open position for dropping the suture.
Figure 14C:
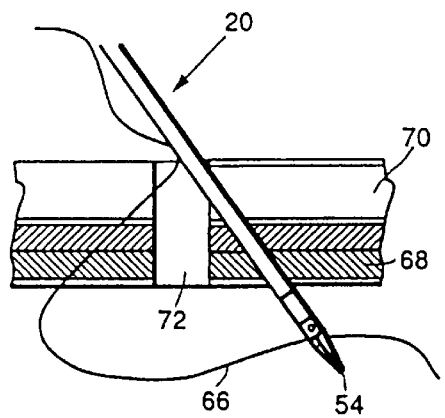
FIG. 14c is a diagrammatic sketch, partly broken away, of the tip of the surgical instrument in the closed position passing through tissue at the other side of the incision and picking up suture.
Figure 14D:
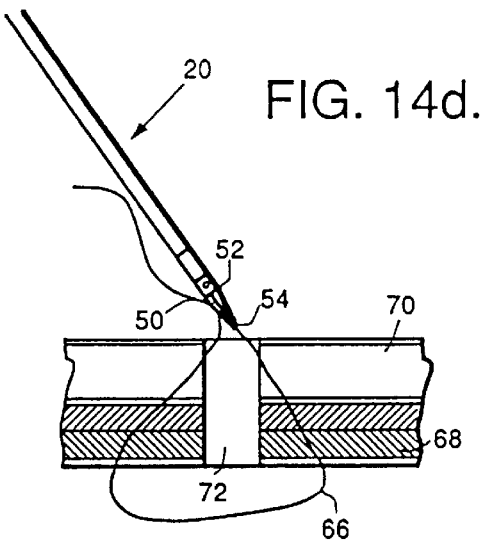
FIG. 14d is a diagrammatic sketch, partly broken away, of the tip of the surgical instrument pulling suture through muscle fascia and peritoneum.
Figure 14E:
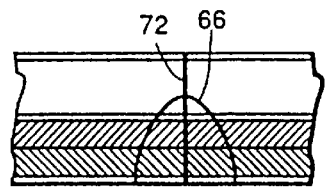
FIG. 14e is a diagrammatic sketch, partly broken away, of the suture tied below the skin to complete closure.

FIGS. 14a through 14e are diagrammatic representations of one example of using the method and laparoscopic instrument 20 with the knife-shape tip 54 of the present invention grasping and passing suture through soft tissue for closure of an incision 72. In FIG. 14a the surgeon grasps the suture material 66 with tip 54 and inserts instrument 20 carrying suture material 66 through the muscle fascia 70 and peritoneum 68 until the tip 54 is seen through the peritoneum by direct camera vision. Subsequently, the surgeon releases the suture 66 by opening jaw 50 and withdrawing the instrument 20 out of incision 72 as shown in FIG. 14b. In FIG. 14c the surgeon then gets instrument 20 and inserts the tip 54 through the muscle fascia 70 and peritoneum 60 opposite the first point of insertion, grasping the suture 66 with jaws 50 and 52 and pulling the suture 66 carried and held by tip 54 outside incision 72 as shown by FIG. 14d whereupon suture 66 is tied below the skin to complete closure of incision 72 as shown by FIG. 14e.

It is to be pointed out that the knife-shaped tip 54 in the above-described method may be replaced with either the chisel-shaped tip 42 or cone-shaped tip 48. Although not shown, it may be envisioned in the above-described method that a second surgical instrument 20 may be inserted through the muscle fascia 70 and peritoneum 68 opposite the first point of insertion grasping the suture 66 with jaws 50 and 52 and pulling the suture 66 held by tip 54 outside incision 72 by either an assistant or the surgeon, resulting in a savings of time for completion of the closure.

By way of example but not of limitation, it has been shown that, by using the present invention during a laparoscopic-assisted vaginal hysterectomy, the total time required for the closure of the two 12 mm and one 10 mm trocar ports has been reduced from 15 minutes (as required by prior surgical procedures) to 3 minutes.

As shown in FIGS. 15–25, additional alternative embodiments of the present invention provide additional advantages for both specific and general applications.

FIG. 15 and 16 show a curved forceps tip 100. The curved forceps tip 100 is curved in an S-shaped curve. The curved tip 100 has two jaws. The lower and movable jaw 102 articulates downwardly from the upper and fixed jaw 104. A pin 106 serves as a pivot point for the lower moving jaw 102.

Both the lower 102 and upper 104 jaws define lateral slots that pass transversely across the inner faces of the jaws 102, 104. The slot 108 present in the lower jaw 102 is oppositely opposed the slot 110 present in the upper jaw. As shown in FIGS. 15 and 16, the slots 108, 110 are positioned toward the proximal end of the jaws 102, 104. As with the small angle 74, as shown in FIG. 12, the slots 108, 110 accommodate suture material 112 so that the two jaws 102, 104 may completely close and provide the sharpest possible tip for tissue penetration. The forwardmost end of the curved forceps tip 100 is exceedingly sharp so as to provide easy and clean penetration of tissues.

The exterior surfaces of the lower and upper jaws 102, 104 are smooth and round to quickly and easily push aside tissue penetrated by the forwardmost end 114 of the tip 100.

The S-shape of the tip 100 provides the surgeon with a better means by which to grasp suture, especially inside the body cavity. The angle the curved tip 100 makes with respect to the probe's shaft 120 (FIG. 17) allows the surgeon to more easily grasp suture that has positioned itself alongside the curved tip 100. In contrast to a straight tip (such as that shown in FIG. 18), the curved tip 100 allows the surgeon to rotate the probe 122 in order to quickly grasp adjacently adjoining suture 112. If the suture material is present immediately adjacent to the curved tip 100, a straight-edged tip would be ill-disposed to grasp material as the surgeon would have to flex the probe within the surgical wound in order to address the suture 112 with the tip. Additionally, the curved tip 100 allows the surgeon to grasp suture in tight confines having difficult angles.

Figure 21:
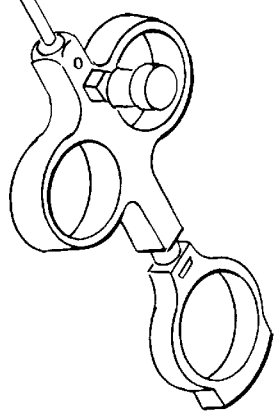
FIG. 21 shows a perspective view of the probe of the present invention having a straight shaft and a syringe-type handle.
Figure 22:
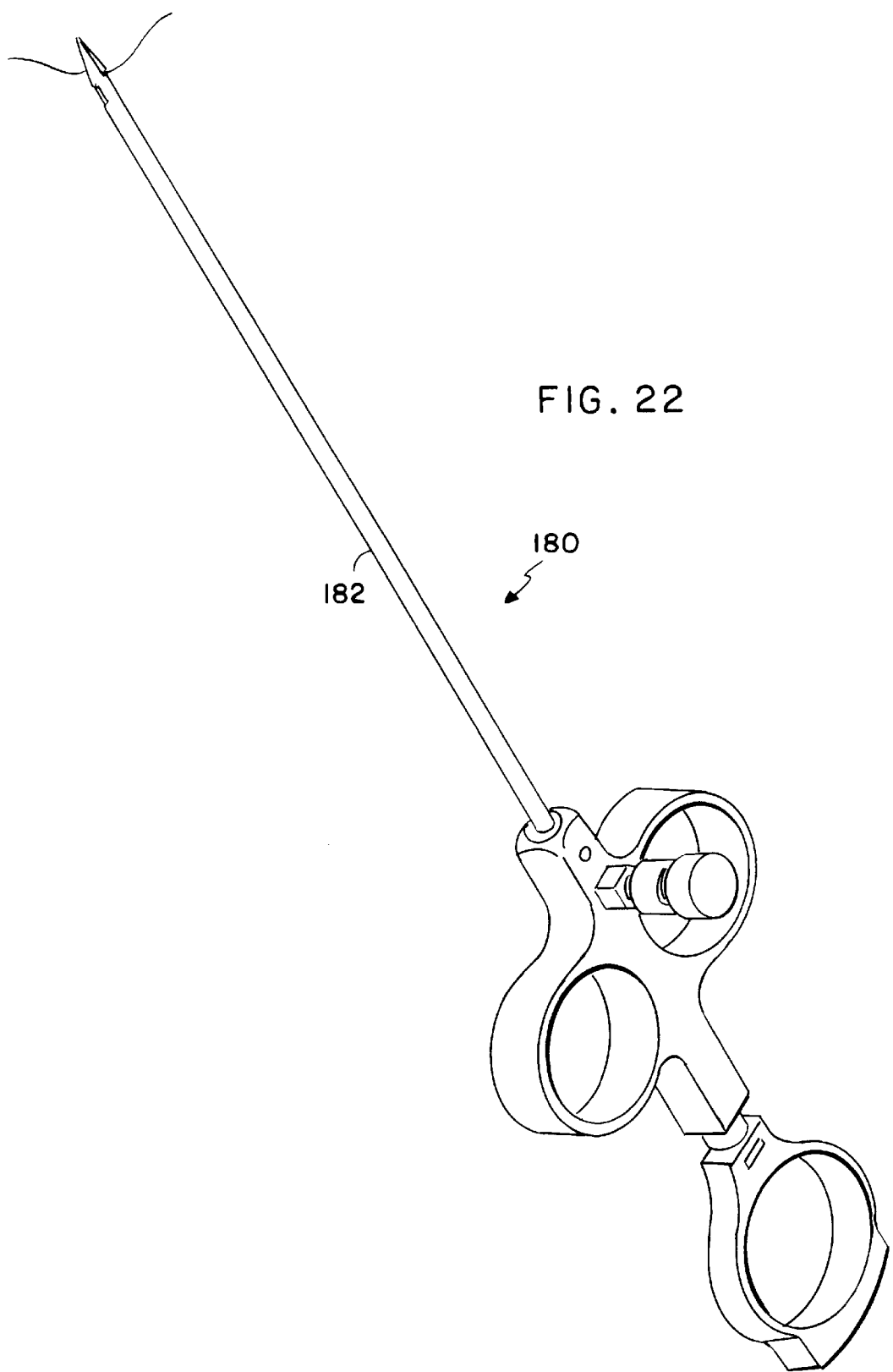
FIG. 22 shows a perspective view of the probe of FIG. 21, having a shorter shaft.

As shown in FIG. 17 as well as FIGS. 21, 22, and 25, the novel handle structure 130 provides an alternative embodiment to that shown in FIGS. 1a and 1b. As opposed to the scissors-type handle structure shown in FIGS. 1a and 1b, the handle structure shown in FIG. 17 is of a syringe type where a surgeon's first and second fingers may hold steady the instrument as a whole with the thumb passing through a thumb loop to control the articulation of the forceps tip.

As shown in FIG. 17, loops for the forefinger and second finger 132, 134, are oppositely opposed about a central stem 136 that provides a solid foundation for the surgeon's hand. The shaft 120 of the probe 122 extends laterally from the central stem and terminates in the forceps tip. Oppositely opposed the shaft 120 with respect to the central stem 136 is a rotatable thumb ring 138. The rotatable thumb ring 138 is freely pivotable with respect to the central stem 136. The thumb ring 138 is connected to a shaft 140 that communicates with the lower moving jaw 102. By moving the thumb ring forward and backward, the lower moving jaw 102 is correspondingly closed and opened. Generally, as it is most advantageous for the surgeon to firmly grasp the handle 130, the lower moving jaw 102 will generally be closed when the thumb ring 130 is moved forward and pressed toward the central stem 135 with its finger loops 132, 134.

A cleaning or flush port 146 is present toward the distal end of the central stem 136. The cleaning port 146 has a cap 142 fitting over a Luer-type fitting 144. In order to provide means by which the internal structures of the probe 122 may be sterilized, the cleaning port may be used to flush out the internal workings and surfaces of the probe 122. To do so, the cap 142 is removed; and a hose having a compatible fitting is attached to the cleaning port's Lueer fitting 144. Cleaning or sterilizing fluid may be then used to rinse the interior of the probe 122, flushing out any particulate matter. This process is advantageously performed before the probe 122, has been autoclaved. Chemical sterilization of the probe 122 can also be performed through the port.

Figure 18:
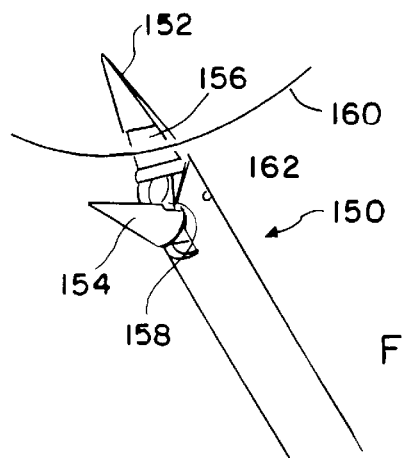
FIG. 18 shows a side perspective view of open forceps jaws connected to a straight tip.

FIG. 18 shows a straight and conical forceps tip 150 having a feed upper 152 and moving lower 154 forceps jaws. Slots 156 and 158 are disposed on the internal jaw faces toward the rear of the jaws 152, 154. As previously described, these oppositely opposed slots provide accommodation for suture material 160 so that the jaws may be completely closed without gap between them for better penetration through tissue.

Figure 19:
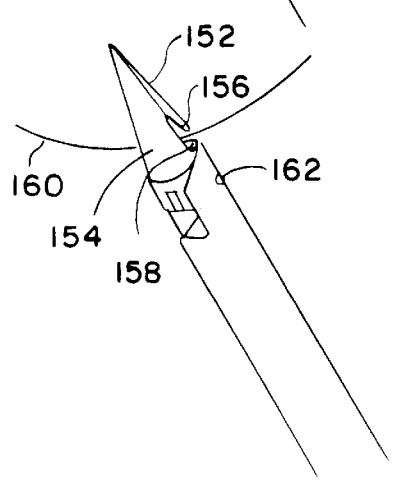
FIG. 19 shows the forceps jaws of FIG. 18 in a closed position, showing the conical shape of the tip.

FIG. 19 shows the straight tip 150 in a closed position carrying suture 160 between the jaws 152, 154, and the slots 156, 158. The lower moving jaw 154 articulates about a pin 162.

FIG. 21 shows a straight forceps tip 150 carrying suture 160, having the handle structure previously described in FIG. 17 and indicated by reference number 130.

Figure 20:
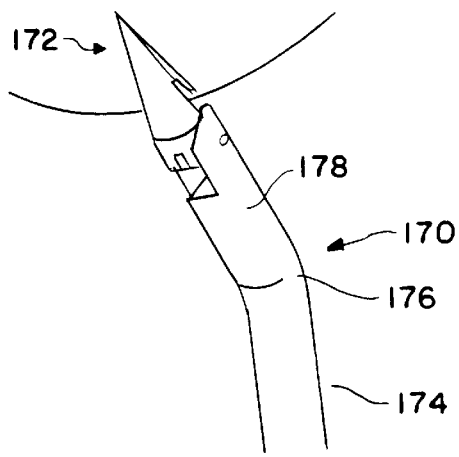
FIG. 20 shows a conical tip forceps with the jaws closed, the tip having a bend in the shaft immediately behind it.

FIG. 20 shows a forceps tip much like that shown in FIG. 18 and 19 save that the shaft 170 immediately preceding the tip 172 has a bend 176 which disposes the tip 172 at an angle to the main portion of the shaft 174. The bend 176 serves to direct the tip 172 away from the major axis of the main portion of the shaft 174. The tip 172 is then directed by the bend 176 to travel along a minor axis defied by the tip 172 and portions of the shaft 178 immediately behind the tip 172.

The tips angling off to one side of the probe shaft, such as those shown in FIGS. 15, 16, and 20, allow the surgeon to tie suture knots more easily and allow access to sites that would otherwise require repositioning of the probe's insertion point and allow the surgeon to avoid awkward hand positioning.

FIG. 22 shows a probe 180 similar to that shown in FIG. 21, the shaft 182 of the probe 180 being relatively shorter an that shown in FIG. 21.

FIGS. 23 and 24 show additional embodiments of forceps tips contemplated for use in the present invention.

In FIG. 23, a transcutaneous grasper tip 190 is shown, having a moving upper jaw 192 and a fixed lower jaw 104. As shown in FIG. 23, serrations 196 are shown on the interior facial portions of the two jaws 192, 194. These serrations 196 are slightly offset to allow complete closure of the transcutaneous grasper tip 190. When the tip 190 is completely closed, the serrations of the lower jaw 194 are immediately adjacent to the serrations 196 on the upper jaw.

When a probe 198, such as that shown in FIG. 25, has a transcutaneous grasper tip 190, as shown in FIG. 23, tissues within the body cavity are more easily grasped due to the increased friction arising from the serrations 196. The probe 198 pierces the muscle fascia and the peritoneum in order to enter the body cavity. Direct camera vision then allows the surgeon to view the progress of the grasper tip 190 inside the body cavity. When tissue of interest to the surgeon needs to be grasped (for possible extraction or positioning), the grasper tip 190 is opened and situated on either side of the tissue of interest. The grasper tip 190 is then closed by manipulation of the thumb ring 138. Once grasped by the tip 190, the tissue is then moved into position according to the surgeon's articulations of the probe 198.

The syringe-type handle design shown in FIG. 25 allows great flexibility in positioning the instrument tip within the body cavity with minimal hand movement required by the surgeon. This results in less fatigue for the surgeon and allows the device to have much greater utility. The flexibility of motion generally arises from the freely rotatable thumb rig 138 and the handle 130. It allows the thumb grasping the handle to move independently of the fingers. The handle 130 also allows the surgeon to rotate the instrument freely without releasing his grip. This feature is not as greatly present in the scissors-type handle shown in FIGS. 1a and 1b. Rotating the instrument while maintaining instrument control is useful for general instrument manipulation and special surgical maneuvers such as suture typing.

Materials used to construct the devices set forth herein include surgical stainless steel and the like.

The present invention has been found to facilitate many camera-viewed laparoscopic procedures. By varying the diameter, length and curvature of the shaft, many procedures may be improved compared to previously-existing methods. Laparoscopic port closure and the identification and retraction of ureters during lympadenectomy also advantageously implement the present invention. The same is likewise true for retraction of kidneys and other structures during laparoscopic nephrectomy.

Intra-abdominal suturing, whether by closing of peritoneum or intra-abdominal knot-tying, has benefited from use of the present invention as has laparoscopic port closure (as for the urological uses listed above). In general surgery, the present invention has been found to be advantageously used with respect to laparoscopic port closures and temporary and permanent fixations of hernia mesh. It is contemplated that many other surgical procedures will advantageously use the present inventive methods and instruments as described herein.

Figure 31:
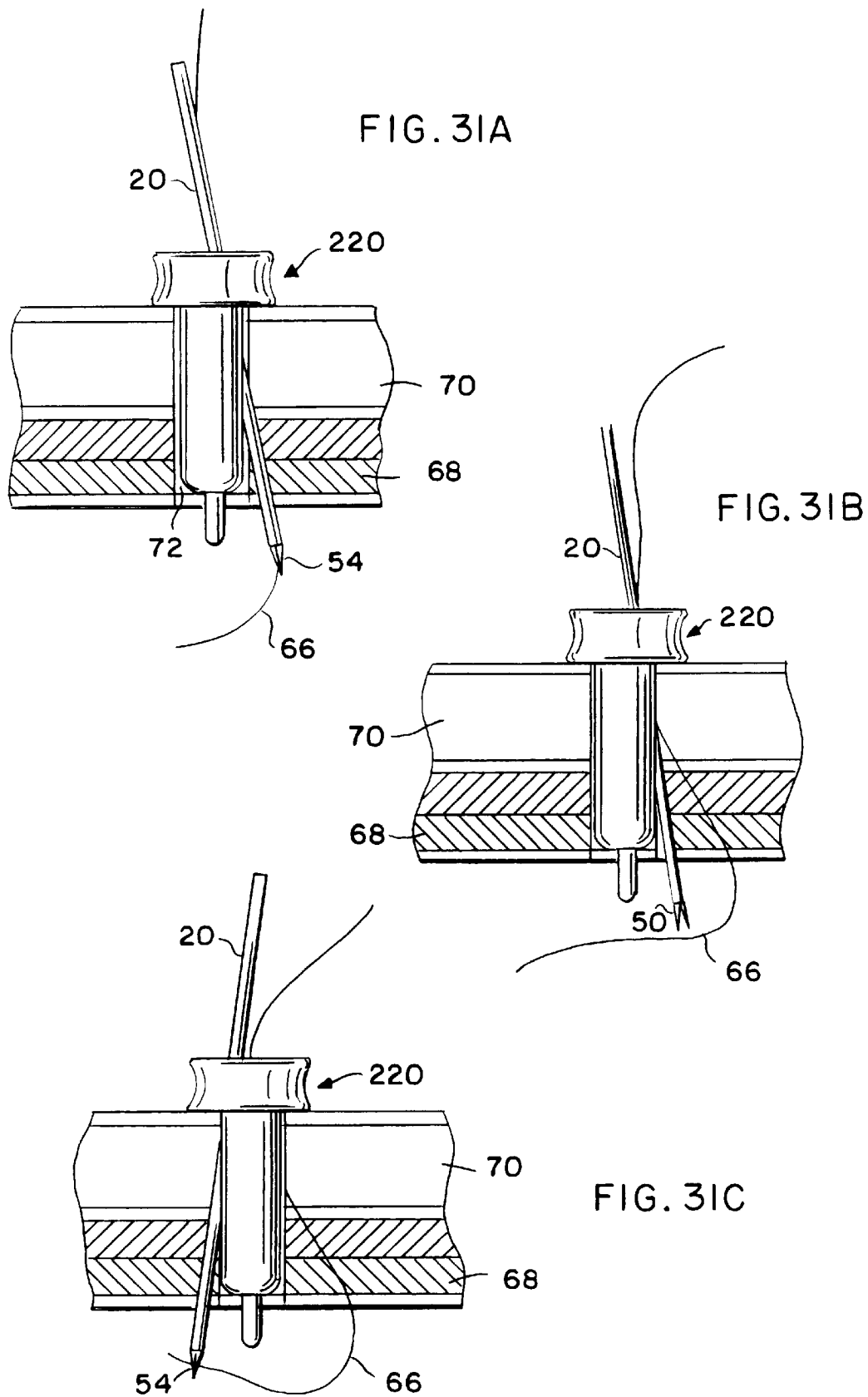
FIG. 31a is a diagrammatic sketch showing the guide of the present invention placed within the wound to be closed receiving the tip of a point of a surgical instrument received within a passageway carrying suture material.
FIG. 31b is a diagramratic sketch of the guide shown in FIG. 31a with the surgical instrument releasing the suture material.
FIG. 31c is a diagrammatic sketch showing the guide of FIGS. 31a and 31b with the surgical tool being received in an opposite and adjacent passageway of the guide retrieving the suture material.

As shown in FIGS. 26–33, a specially adapted guide 220 can be used in the suturing procedure discussed above, and its application is demonstrated in FIG. 31a–31c. The guide 220 provides the surgeon a device and methodology for accurately and precisely positioning and removing the suture material 66 in or from the patient's body where desired.

Figure 26:
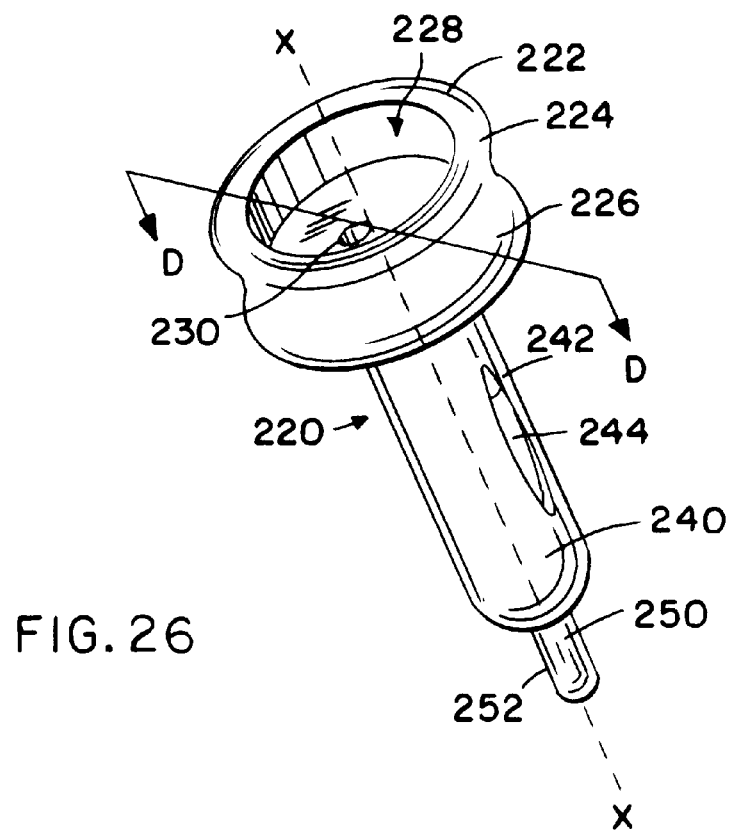
FIG. 26 is a perspective view of the insertable grasping probe guide of the present invention having a longitudinal axis x.

The guide 220 has a longitudinal axis shown in FIG. 26 and is generally symmetrical about its x axis. Its proximal end 222 defines an integrally-formed annulus 224 which serves as a gripping area for the surgeon with a concave, radially disposed surface 226 which further assists the surgeon in gripping and holding the guide 220. The concave surface 226 may be smooth or knurled.

A top cylindrical recess 228 in the annulus 224 exposes two entry holes 230 to generally linear passageways 232 through the guide 220. The passageways 232 are appositely adjacent, and each forms a diverging angle alpha of approximately 10° with the longitudinal axis x but can range over a number of angles less than 90°. Optimally, the angle is 9.6° for an overall guide 220 length of 2.7 inches. The entry holes 230 are located along a diameter line and are approximately 0.2 inches from center hole to center hole but may vary between 0.1 inches to 1 inch depending upon the desired angle x. The holes are sized to receive the surgical instrument to be used.

In use, the annulus 226 stands proud of the wound but has an undersurface or lip 234 which is adjacent the wound to be sutured. The recess 228 provides access to the entry holes 230 and passageways 232 yet prevents unwanted body fluids from obscuring the entry holes 230. The lip 234 prevents the guide 220 from sliding into the wound and, therefore, should be sized to be of a greater diameter than that of the open wound to be sutured.

A distal portion 240 of the guide 220 may be slightly tapered although it may not be necessary. Tapering allows for greater ease of insertion into the wound. The passageways 232 have exit holes 242 in the distal portion 240 and may include a flaring 244 or tapering. The holes 230 and 242 to passageways 232 are sized to receive the surgical tools to be used and optimally may be less than one-quarter inch in diameter.

An extending finger 250 is adjacent the distal portion 240 and primarily serves as an alignment or bearings indicator for the surgeon viewing the procedure by camera. It is helpful to actually see the relative positioning of the guide 220 by its extending finger 250 which extends far enough down to where the viewing is taking place during the operation. It is round on its distal end 252 for ease of insertion.

An index 254 may be located between the two entry holes 230 to visually advise the surgeon to line up the index 254 with the cut of the wound to ensure that suturing takes place at approximately 90° to the sliced walls of flesh.

The entire guide 220 can be integrally molded out of high-density polyethylene or other comparable material which is durable and medically inert or machined from stainless steel.

Figure 27:
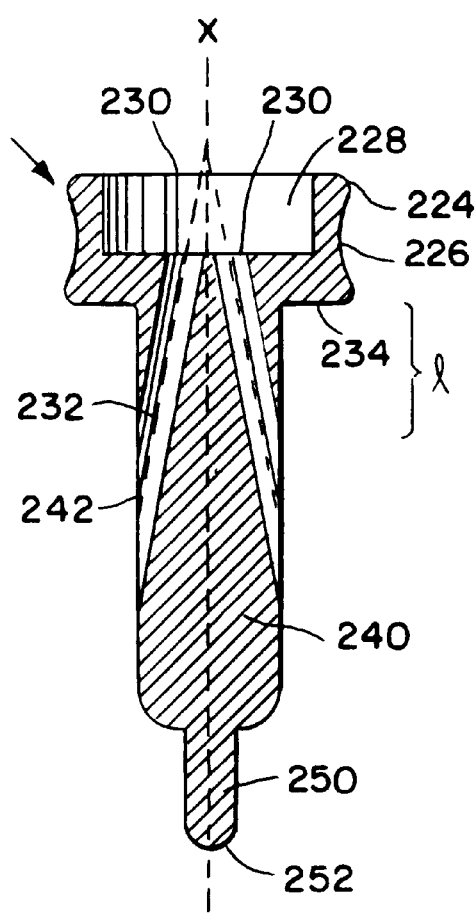
FIG. 27 is a cross-sectional view of the guide taken along the line D—D in FIG. 26 and FIG. 29.
Figure 29:
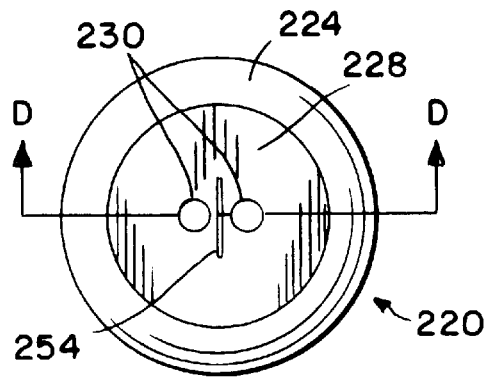
FIG. 29 is a top plan view of the guide shown in FIGS. 26, 27, and 28.
Figure 28:
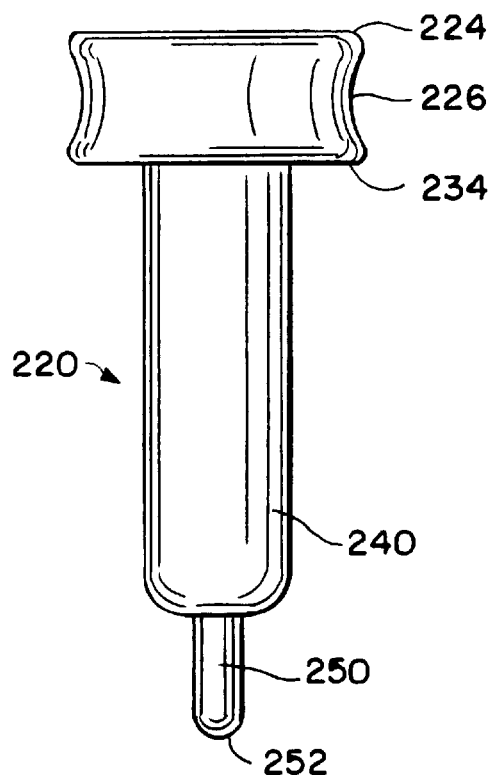
FIG. 28 is a side elevational view of the guide shown in FIGS. 26 and 27.
Figure 30:
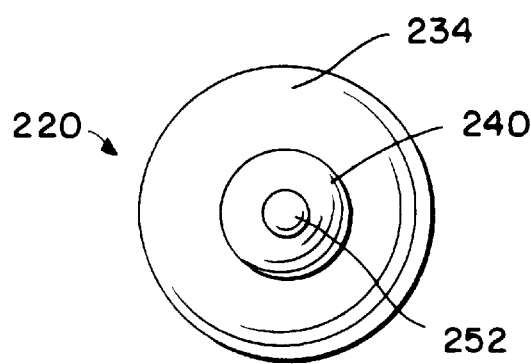
FIG. 30 is a bottom plan view of the guide shown in FIGS. 26, 27, 28 and 29.

The distance L as shown in FIG. 27 between the undersurface 234 of the annulus 224 and the exit holes 242 in the distal portion 240 is a function of the patient's anatomy, in particular his or her body fat composition. Ideally, the surgeon desires to reach a particular layer to suture which may vary from patient to patient. Therefore, varying sized guides 220 are anticipated with the length L being different and ranging between 0.5 inches and 8 inches. Also, the overall length of the distal portion 240 may vary depending upon the patient's anatomy, but an optimum length ranges between 1.5 to 4 inches.

It is also possible to use the guide 220 of the present invention with only one passageway 232; however, the surgeon would have to rotate the guide 220 180° to retrieve the suture material once the suture material was deposited.

As can be seen in FIGS. 31a–31c, the guide greatly assists in the procedure described above for FIGS. 14a–e. More particularly, the guide 220 is placed with the distal end 240 through the skin incision, muscle fascia, and peritoneum so that the finger distal tip 252 appears in the view of the laparoscope. The guide 220 is oriented so that the holes 230 in the guide 220 are in the caudad-to-cephalad position.

The fascial closure instrument 20 (or 122) is inserted with suture in its grasp through the cephalad hole in the guide 220 and observed to exit through the peritoneum by laparoscopic view.

The suture is then released and the instrument 20 (or 122) withdrawn from the guide 76. The instrument 20 is placed in the caudad hole of the guide and watched by laparoscopic view to exit through the peritoneum in the caudad position, therefore passing through fascia and peritoneum on the caudad side of the incision. The guide 220 is then withdrawn up on the shaft of the instrument 20, allowing the instrument free mobility to grasp the suture that had been left with the first passage.

The suture is withdrawn through the hole made by the instrument 20. The guide 220 is then withdrawn from the suture completely. The suture is then tied by standard techniques, thus encompassing the fascia and peritoneum in a mass closure under the skin.

The guide 220 allows the suture instrument through fascia and peritoneum and mass closure of all incisions greater than 5 mm and the identification of the position of a trocar placement for use in occluding a trocar site.

It also provides for placement in a trocar or other abdominal wall site where a vessel, such as an inferior epigastric, has been lacerated and allows passage of the instrument 20 for suturing of tissue around the vessel to occlude the vessel and stop bleeding and for fascial closure of any abdominal incision.

It provides for a method to obtain a measured amount of fascia and peritoneum for laparoscopically controlled mass closure by varying the length of the tool and the angle of the guide holes. By varying the tip length and the length of the overall guide 220, visualizing the guide 220 itself, and placing the guide properly in incisions intra-abdominally, closure of wounds in an individual of any weight is made possible.

By providing for the tip design, visualization of the guide 220 through the fascia and peritoneum is possible by laparoscopic visualization, for repair of vascular damage to abdominal wall in any area.

As can be seen by inspection of the Figures, particularly FIGS. 15, 20, and 27, some surgical instruments that do not maintain a straight or linear configuration could not use the guide 220 with its long, straight passages.

Alternative embodiments to the suture guide shown in FIGS. 26 et seq. are shown in FIGS. 32–35.

Figure 32:
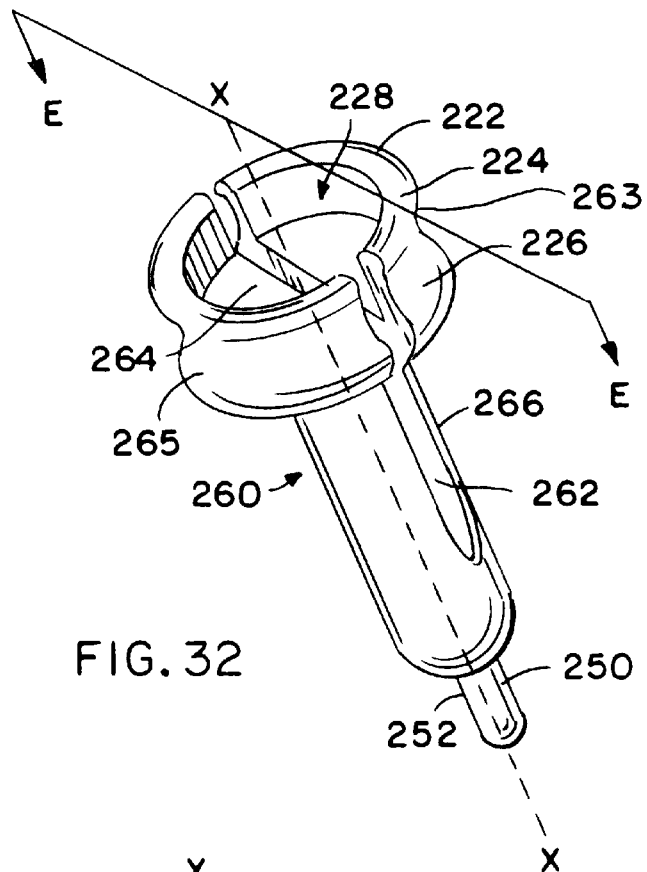
FIG. 32 is a top perspective view of an alternative embodiment of the probe guide shown in FIG. 26.
Figure 33:
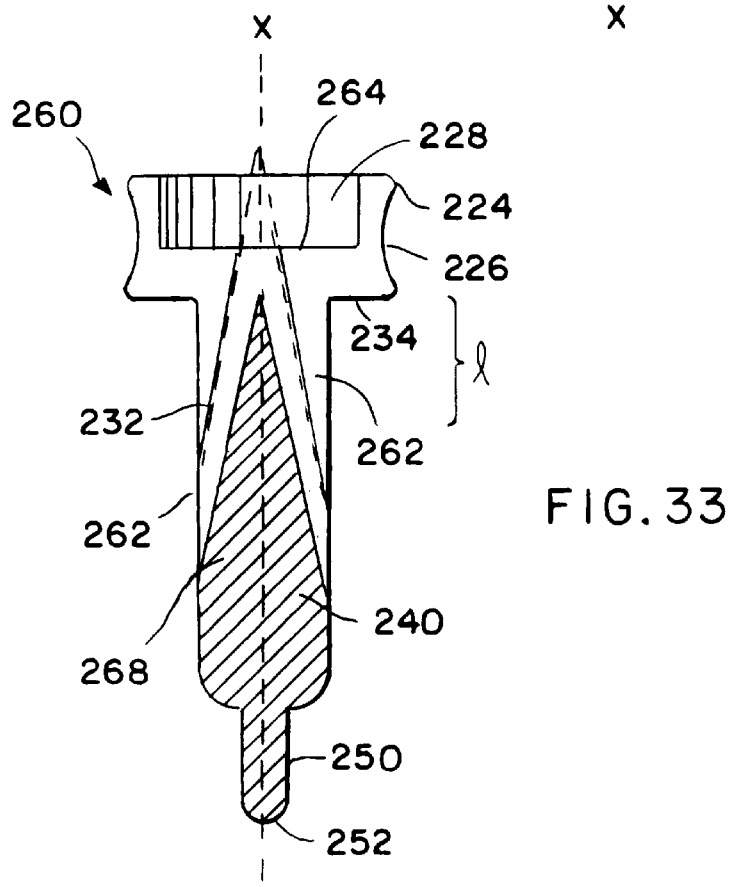
FIG. 33 is a cross section view of the probe guide of FIG. 32 taken along line E—E.

A first alternative embodiment is shown in FIGS. 32 and 33 where the suture guide 260 has a slot 262 allowing passage of the surgical instrument through the guide and into the flesh to be sutured. The top 264 of the slot 262 provides the suture and surgical instrument with access to the surgical wound while the side 266 of the slot 262 has the adjacent flesh ready for suturing by the surgical instrument.

In most other aspects, the suture guide shown in FIG. 32 is similar to that as shown in FIGS. 26 et seq. and like elements are labeled with like reference numbers. Note should be taken that proxial end 222 is bisected by slot 262 to form two wings 263, 265. The wings so formed extend perpendicularly to the longitudinal axis x and can allow a surgeon to more easily manipulate the suture guide 260.

The cross section view shown in FIG. 33 shows the central supporting portion 268 which guides the suturing surgical instrument to the adjacent flesh of the surgical wound. One advantage of the embodiment shown in FIGS. 32 and 33 is that suturing surgical instruments having bent tips or the like (such as those shown in FIGS. 15, 16, and 20) may realize the advantages of using a suture guide that might otherwise be prevented if the passage through which the suturing surgical instrument had to pass could not accommodate the bent, or curved, tips.

Figure 34:
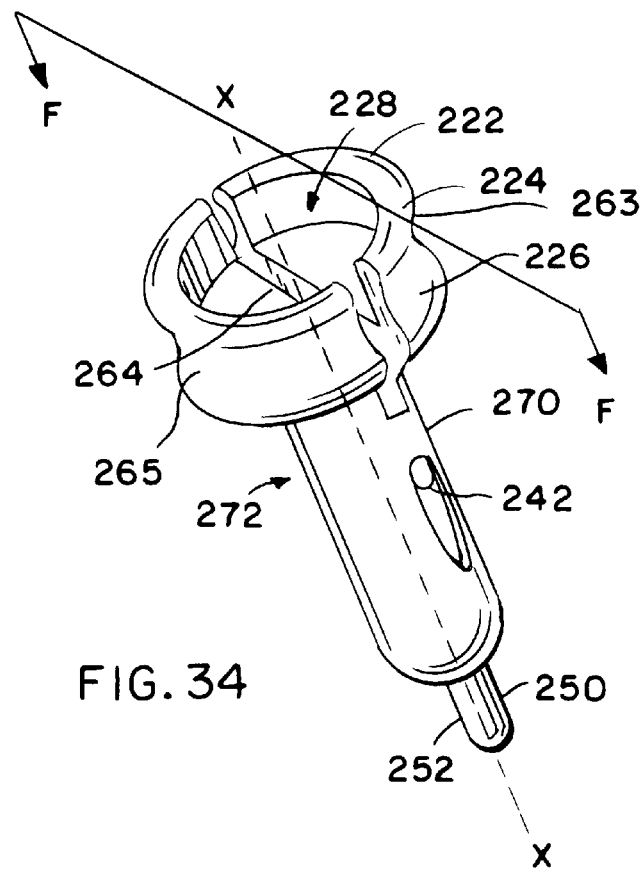
FIG. 34 is a top perspective view of an alternative embodiment of the probe guide shown in FIG. 32.
Figure 35:
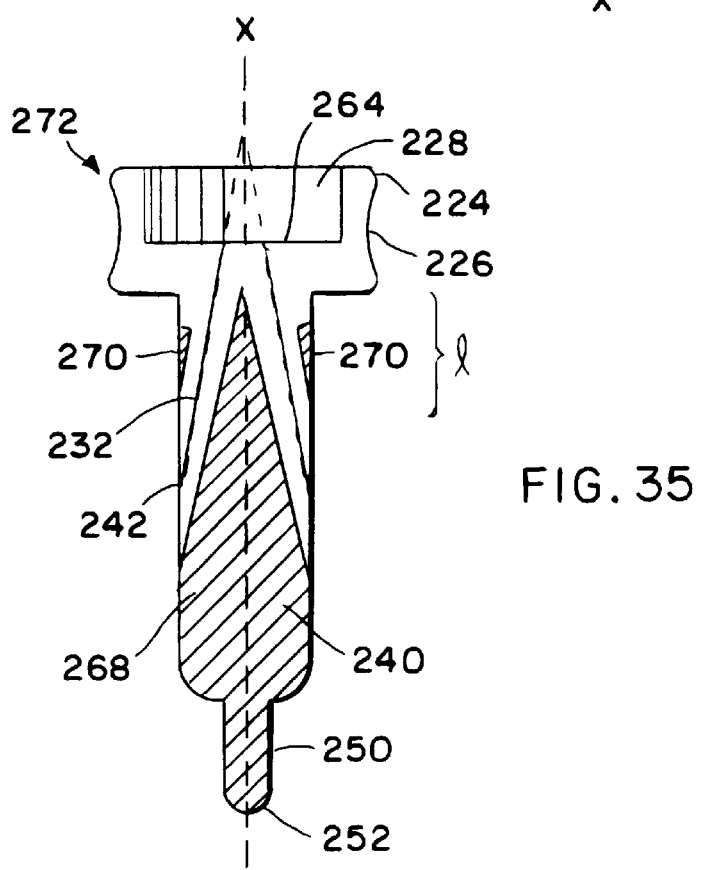
FIG. 35 is a cross section view of the probe guide of FIG. 34 taken along line F—F.
Figure 36:
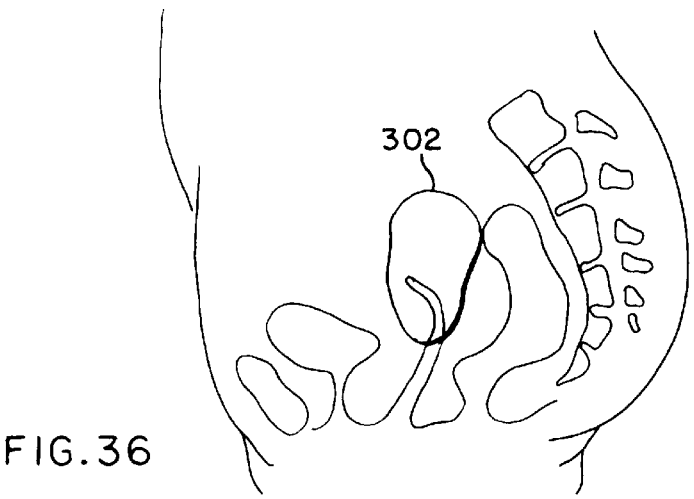
FIG. 36 is a side view of the female reproductive system showing a retroverted uterus.

Similarly, a second alternative embodiment of the suture guide shown in FIGS. 26 et seq. is shown in FIGS. 34 and 35. Like elements are labeled with like reference numbers; and like in the embodiments shown FIGS. 32 and 33, a top slot 264 is present; however, the exit holes 242 are maintained. Guide barriers 270 are present in the alternative embodiment shown in FIGS. 34 and 35. The suture guide 272 may still allow suturing surgical instruments such as those in FIGS. 15, 16, and 20 to use a suturing guide; however, the guide barriers 270 allow the surgeon more guidance during the insertion process of the surgical instrument into the suture guide 272.

Now referring to FIGS. 36–45, a method may be described for suturing ligaments within a person's body using the laparoscopic, suture passer instrument 20. In particular, the procedure described is for retracting and reinforcing the ligament attached to a woman's uterus, to reposition and stabilize the uterus to eliminate pain associated with its misalignment. Patients with severe pelvic pain, pain with intercourse, and severe painful menstruation may suffer from a backward-bending or a retroverted uterus 302 (See FIG. 36). If the uterus 302 can be suspended and placed in its proper position, these pains may resolve. Elevating the uterus 302 improves venous drainage and improves uterine drainage at time of menstrual flow. Collision dyspareunia is avoided since the cervix is pulled up out of the way.

Figure 37:
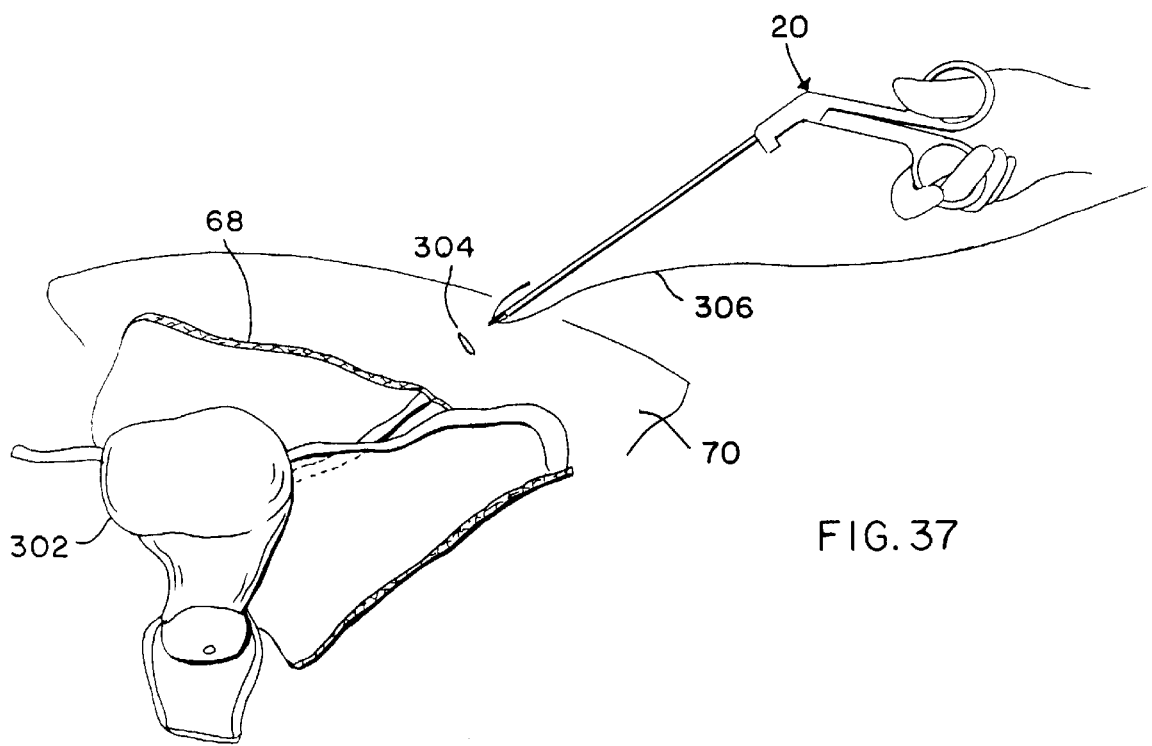
FIG. 37 is a view of entering a woman's body and pelvis, and showing the suturing tool in a preperitoneal position.
Figure 38:
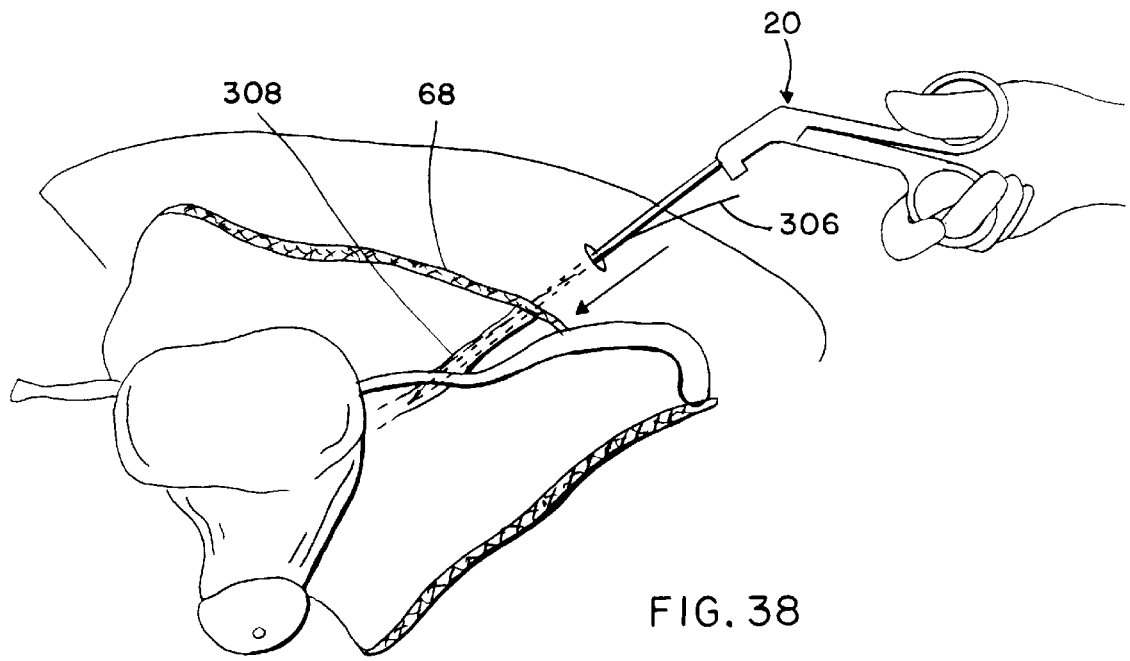
FIG. 38 is a view of inserting the tool into the round ligament, and pushing suture along the axial length.

Referring now to FIG. 37, first a small skin incision (not shown) is made, overlying the area of the inguinal canal. Permanent suture material 306 is then introduced using the needle-point suture passer 20 through the small skin incision, and passed through a first point 304 in the muscle fascia 70, but not through the peritoneum, or broad ligament 68, in order to introduce the suture 66 within the preperitoneal space overlying the round ligament 308. As shown in FIG. 38, the needle-point suture passer 20 with the permanent suture 306 is passed through the preperitoneal space and into the round ligament 308, preferably at its test section where it is attached to the peritoneum 68.

Figure 39:
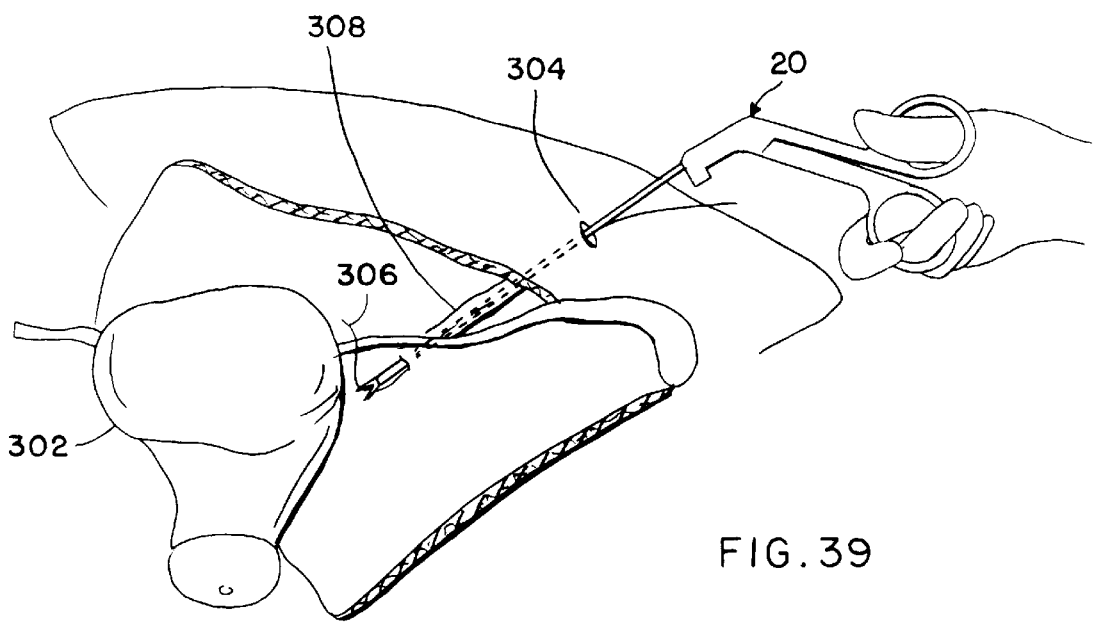
FIG. 39 is a view of exiting the ligament, and dropping the suture.
Figure 40:
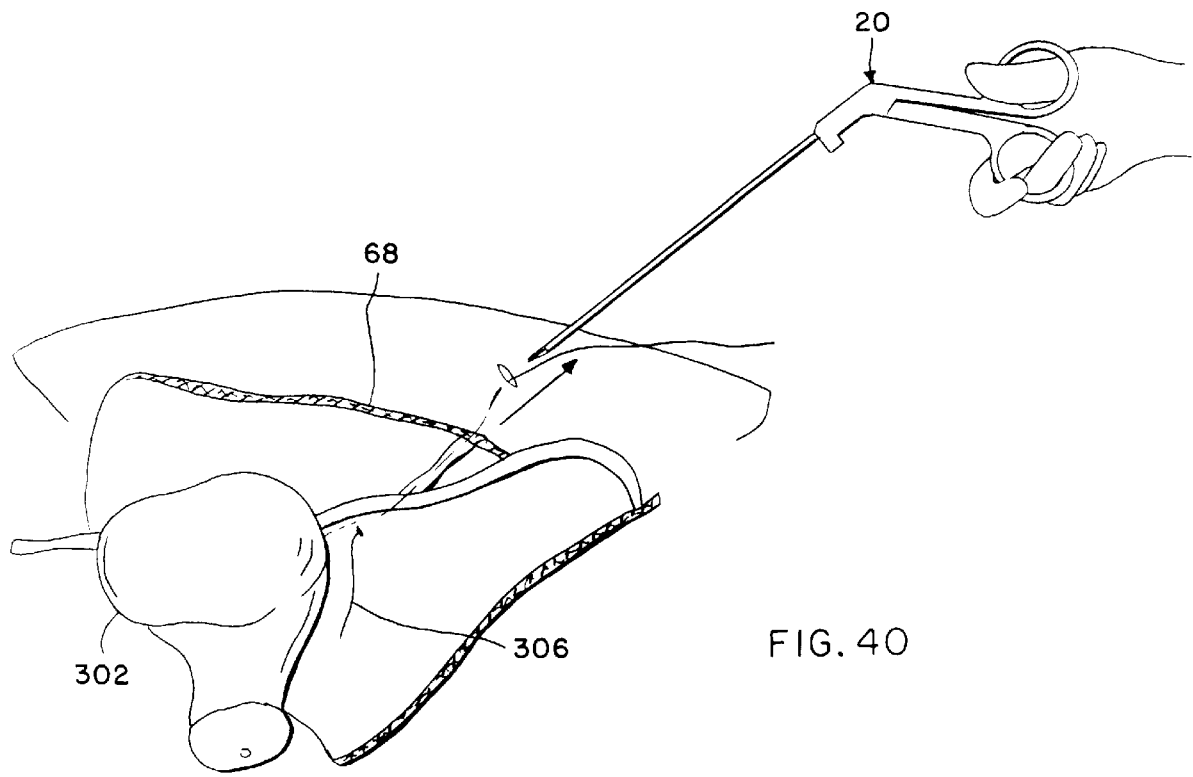
FIG. 40 is a view of withdrawing the tool without the suture.
Figure 41:
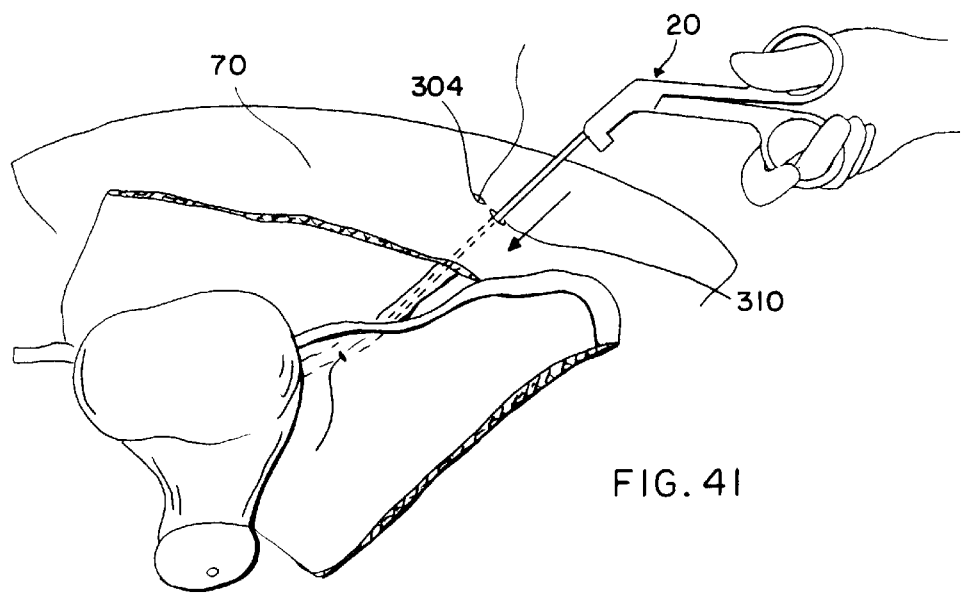
FIG. 41 is a view of reinserting the tool into the round ligament, and pushing it along a second time without the suture.

Referring to FIG. 39, approximately one to two centimeters from the uterus 302 the needle-point suture passer 20 exits at a first point from the round ligament 308 with the suture 306. The suture 306 is dropped, and the needle-point suture passer 20 is withdrawn from the abdominal cavity (see FIG. 40). The suture passer 20 (without suture) is reintroduced through the same skin incision (not shown) at a second point 310 in the fascia 70 (see FIG. 41), so a fascial bridge 312 will be created to fix the suspension (See FIG. 44).

Figure 42:
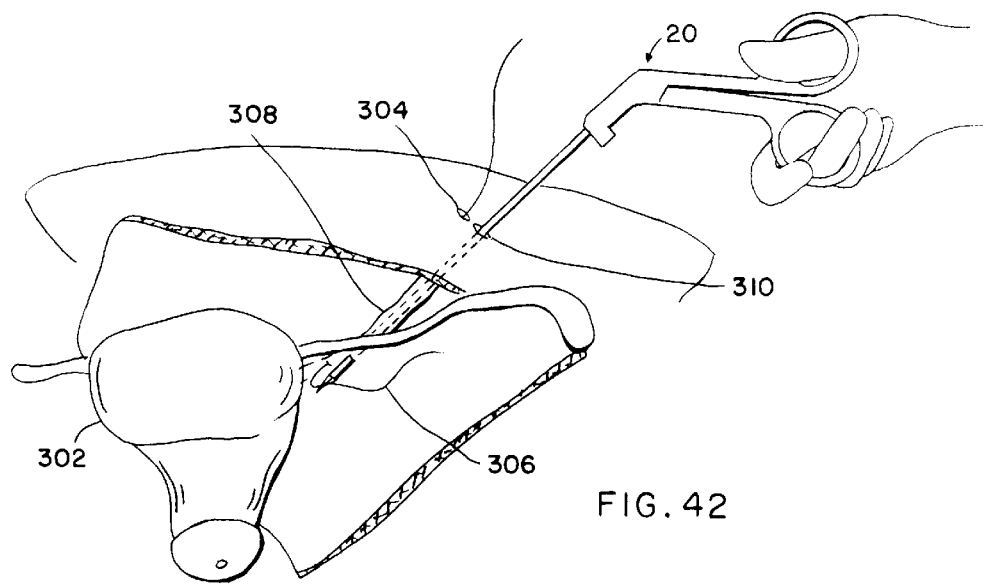
FIG. 42 is a view of exiting the ligament, and picking up the suture.

FIG. 42 shows needle-point suture passer 20 being passed along the round ligament 308 until a second point one to two centimeters from the uterus 302 is reached.

Figure 43:
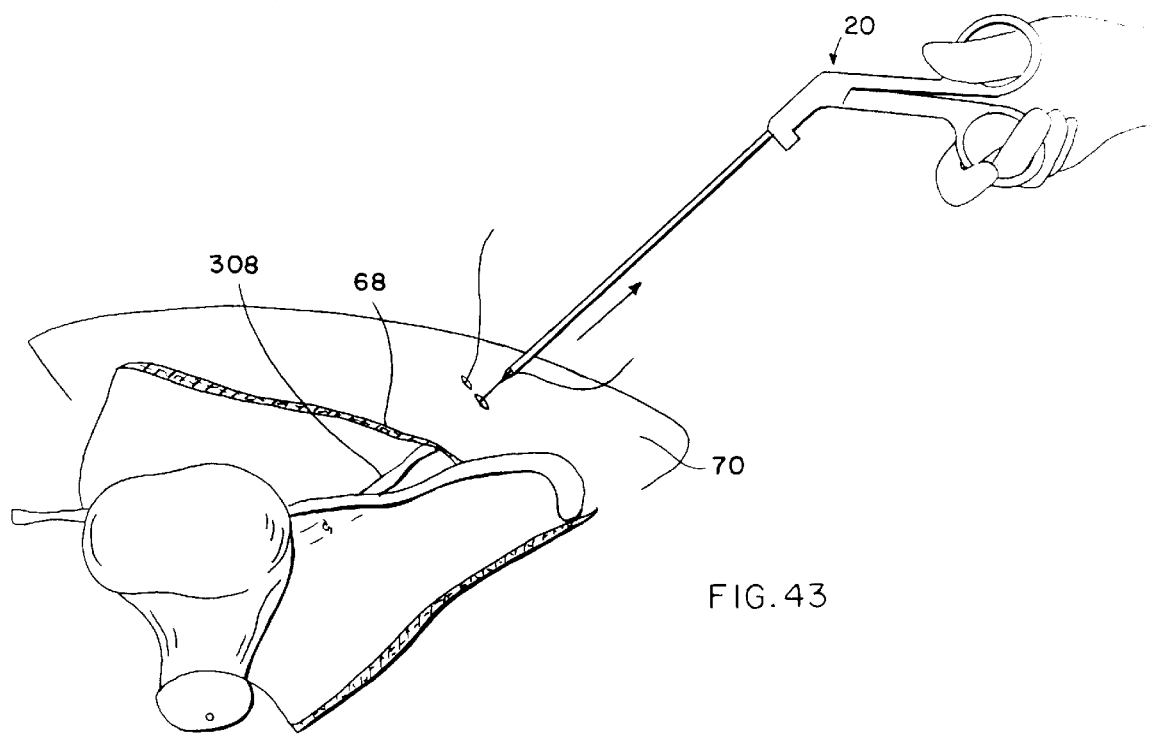
FIG. 43 is a view of withdrawing the tool, and pulling the suture along the axial length of the ligament.
Figure 44:
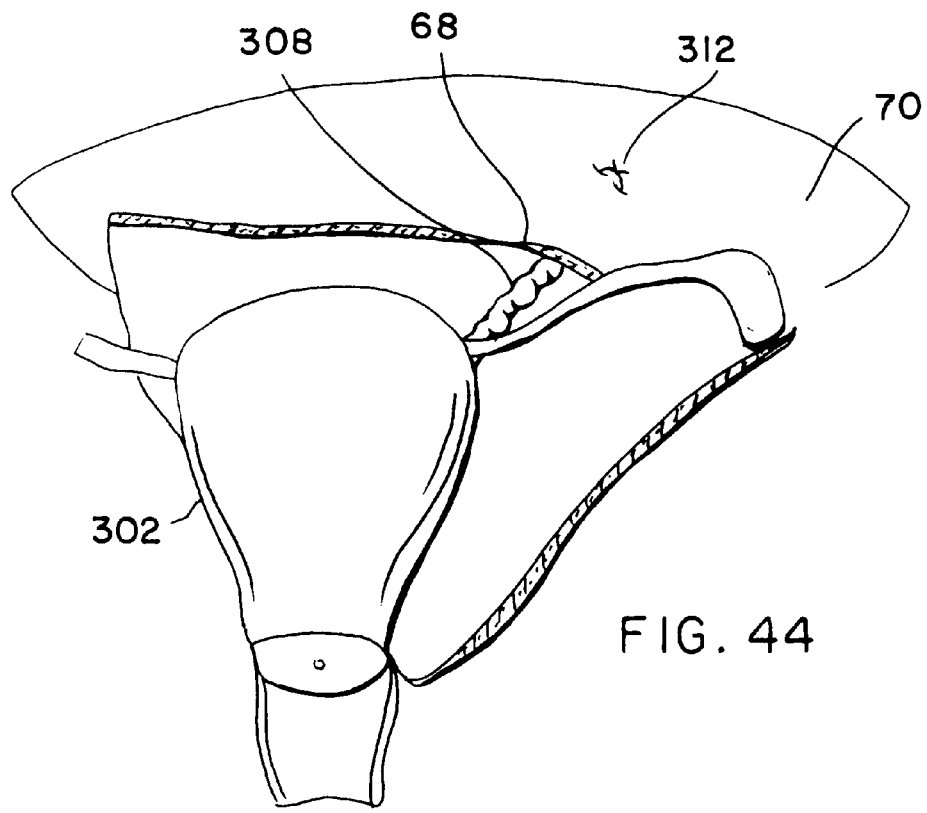
FIG. 44 is a view of the shortened, thickened and reinforced ligament and properly suspended uterus.
Figure 45:
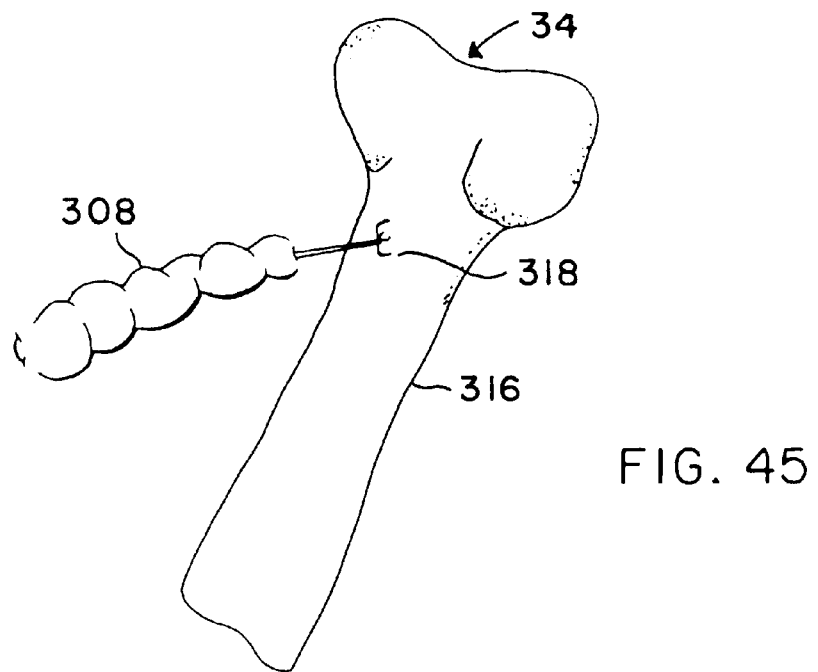
FIG. 45 is a view of attaching the suture to a bone.

The needle-point suture passer 20 then grasps the suture 306 and retrieves it within the round ligament 308 (FIG. 43). Then, the needle-point suture passer 20 is used to pull the truncated and thickened round ligament 308 within the peritoneum 68, providing the preperitoneal 68 suspension of the uterus 302 (FIG. 44).

The round ligament 308 has now been thickened, shortened, and is used in this manner to support the uterus 302 in a neutral position. The opposite side was previously truncated and suspended with this technique, the suture similarly applied externally under the skin and above the fascial bridge 312 that was created. The final effect of the suspension is shown in FIG. 44, with the uterus 302 well placed in a neutral position. In this manner, venostasis will not occur, collision dyspareunia will not be experienced, and menstrual flow will be easier. The preperitoneal uterine suspension using the needle-point suture passer 20 is simple to perform, efficacious, and of great benefit to patients.

Besides using the fascial bridge 312 to attach the suture material 306 to the peritoneum, other methods of fixing ligaments are also contemplated. For example, ligaments reinforced with suture may be attached to any anatomical anchoring point 314 such as a bone 316, or a medical device 318 anchored to a bone 316. See FIG. 41A.

Although the above procedure for suturing ligaments describes repositioning and stabilizing a woman's uterus, other applications are contemplated. For example, the new methods may have application in certain knee surgeries, and in breast-lift procedures.

It is understood that the exemplary methods described herein and shown in the drawings represent only presently preferred embodiments of the invention. Indeed, various modifications and additions may be made to such embodiments without departing from the spirit and scope of the invention. These and other modifications and additions may be obvious to those skilled in the art and may be implemented to adapt the present invention for use in a variety of different applications.

What is claimed is:

1. A method of suturing ligaments within a person's body comprising the steps of:
    (a) laparoscopically entering the person's body with a tool having a sharp tip bearing suture material for suturing ligaments;
    (b) inserting said tool into the ligament to be affected along its axial length, and pushing said suture material through the axial length;
    (c) pulling said suture material exteriorly from the ligament in a direction generally opposite of said suture material's point of entry to the ligament causing the ligament to retract along its length; and
    (d) attaching said suture material within the body at a point generally in proximity to said suture's original point of entry into the ligament, whereby the ligament retracted along its length is reinforced within the person's body.

2. The method of claim 1, wherein inserting said tool into the ligament along its axial length includes its thinnest section.

3. The method of claim 1, wherein inserting said tool into the ligament along its axial length includes near the supporting point of an internal organ.

4. The method of claim 1, wherein attaching said suture material is to an anatomical anchoring point.

5. The method of claim 1, wherein attaching said suture material is to a medical device.

6. The method of claim 5, wherein the medical device is anchored to a bone.

7. The method of claim 1, wherein inserting said tool into the ligament to be affected is the round ligament attached to a woman's uterus.

8. A method of suturing ligaments within a person's body comprising the steps of:
    (a) laparoscopically entering the person's body at a first point in the body with a tool having a sharp tip bearing suture material for suturing ligaments;

(b) inserting said tool into the ligament to be affected along its axial length, and pushing said suture material through the axial length;

(c) exiting the ligament at a first point in the ligament and dropping off the suture material;

(d) withdrawing the tool from the ligament;

(e) laparoscopically entering the person's body at a second point in the body with the tool;

(f) inserting the tool into the ligament and pushing the tool along the axial length of the ligament;

(g) exiting the ligament at a second point in the ligament and grasping the suture material;

(h) withdrawing the tool from the ligament; and (i) pulling the suture material exteriorly from the ligament in a direction generally opposite of said suture material's point of entry to the ligament causing the ligament to retract along its length; and (j) attaching said suture material within the body at a point generally in proximity to said suture's original point of entry into the ligament, whereby the ligament retracted along its length is reinforced within the person's body.

9. The method of claim 8, wherein inserting said tool into the ligament along its axial length includes its thinnest section.

10. The method of claim 8, wherein inserting said tool into the ligament along its axial length includes near the supporting point of an internal organ.

11. The method of claim 8, wherein attaching said suture material is to an anatomical anchoring point.

12. The method of claim 8, wherein attaching said suture material is to a medical device.

13. The method of claim 12, wherein the medical device is anchored to a bone.

14. A method of investing suture within ligaments in a person's body comprising the steps of:

(a) entering the person's body with suture materials for suturing ligaments;

(b) inserting the suture material into the ligament to be affected along its axial length, and pushing said suture material through the axial length;

(c) pulling said suture material exteriorly from the ligament in a direction generally opposite of said suture material's point of entry to the ligament causing the ligament to retract along its length; and (d) attaching said suture material within the body at a point generally in proximity to said suture's original point of entry into the ligament, whereby the ligament retracted along its length is reinforced within the person's body.

15. The method of claim 14, wherein entering the person's body is laparoscopically with a tool having a sharp tip bearing the suture material.

16. The method of claim 15, wherein inserting the suture material is with the tool.

17. A method of suturing ligaments within a person's body comprising the steps of:

(a) entering the person's body at a first point in the body with suturing material for suturing ligaments;

(b) inserting the suture material into the ligament to be affected along its axial length, and pushing said suture material through the axial length;

(c) exiting the ligament at a first point in the ligament and dropping off the suture material;

(d) entering the person's body at a second point in the body with the tool;

(e) exiting the ligament at a second point in the ligament and grasping the suture material;

(f) pulling the suture material through the axial length of the ligament;

(g) pulling the suture material exteriorly from the ligament in a direction generally opposite of said suture material's point of entry to the ligament causing the ligament to retract along its length; and (h) attaching said suture material within the body at a point generally in proximity to said suture's original point of entry into the ligament, whereby the ligament retracted along its length is reinforced within the person's body.

18. The method of claim 17, wherein entering the person's body is laparoscopically with a tool having a sharp tip bearing the suture material.

19. The method of claim 18, wherein inserting the suture material is with the tool.

* * * * *